US009005122B2

(12) United States Patent
Addington et al.

(10) Patent No.: US 9,005,122 B2
(45) Date of Patent: *Apr. 14, 2015

(54) DEVICE WITH PASSIVE VALVE TO BLOCK EMESIS AND/OR REFLUX AND ASSOCIATED SYSTEM AND METHOD

(71) Applicant: Pneumoflex Systems, LLC, Melbourne, FL (US)

(72) Inventors: W. Robert Addington, Melbourne Beach, FL (US); Stuart P. Miller, Indialantic, FL (US)

(73) Assignee: Pneumoflex Systems, LLC, Melbourne, FL (US)

( * ) Notice: Subject to any disclaimer, the term of this patent is extended or adjusted under 35 U.S.C. 154(b) by 258 days.

This patent is subject to a terminal disclaimer.

(21) Appl. No.: 13/767,900

(22) Filed: Feb. 15, 2013

(65) Prior Publication Data
US 2014/0235957 A1 Aug. 21, 2014

(51) Int. Cl.

| | |
|---|---|
| *G06F 19/00* | (2011.01) |
| *A61B 5/00* | (2006.01) |
| *A61M 39/22* | (2006.01) |
| *A61B 5/03* | (2006.01) |
| *A61M 16/14* | (2006.01) |
| *A61J 15/00* | (2006.01) |
| *A61M 25/00* | (2006.01) |
| A61B 5/0488 | (2006.01) |
| A61B 5/08 | (2006.01) |
| A61B 5/145 | (2006.01) |
| A61B 17/00 | (2006.01) |
| A61M 25/10 | (2013.01) |

(52) U.S. Cl.
CPC .............. *A61M 39/22* (2013.01); *A61B 5/037* (2013.01); *A61B 5/0488* (2013.01); *A61B 5/0823* (2013.01); *A61B 5/14539* (2013.01); *A61B 5/687* (2013.01); *A61M 16/14* (2013.01); *G06F 19/34* (2013.01); *A61B 5/7282* (2013.01); *A61B 5/04884* (2013.01); *A61J 15/0046* (2013.01); *A61B 5/4211* (2013.01); *A61M 25/0029* (2013.01); *A61B 2017/00827* (2013.01); *A61M 2025/0002* (2013.01); *A61M 2025/1052* (2013.01); *A61B 2562/0247* (2013.01)

(58) Field of Classification Search
None
See application file for complete search history.

(56) References Cited

U.S. PATENT DOCUMENTS

| | | | | |
|---|---|---|---|---|
| 4,168,703 | A | * | 9/1979 | Kenigsberg .................. 600/561 |
| 4,214,593 | A | | 7/1980 | Imbruce et al. |
| 4,613,323 | A | | 9/1986 | Norton et al. |

(Continued)

FOREIGN PATENT DOCUMENTS

| | | |
|---|---|---|
| DE | 2412553 | 9/1975 |
| EP | 0 694 284 | 1/1996 |

(Continued)

*Primary Examiner* — William Thomson
*Assistant Examiner* — Davin Sands
(74) *Attorney, Agent, or Firm* — Allen, Dyer, Doppelt, Milbrath & Gilchrist, P.A.

(57) ABSTRACT

A device to block emesis and/or reflux includes a tube insertable into the esophagus. A valve is carried by the tube and includes a flexible sheath having an upper edge secured onto the tube and an unsecured lower circumferential edge and configured such that upon contact with emesis and/or reflux from the stomach, the flexible sheath opens in a concave configuration towards the stomach and the unsecured lower circumferential edge engages the esophageal wall and blocks emesis and/or reflux from the stomach passing into the esophagus past the valve.

13 Claims, 16 Drawing Sheets

(56) References Cited

U.S. PATENT DOCUMENTS

| | | |
|---|---|---|
| 4,752,286 A | 6/1988 | Okada |
| 4,976,261 A | 12/1990 | Gluck et al. |
| 4,981,470 A | 1/1991 | Bombeck, IV |
| 5,146,916 A | 9/1992 | Catalani |
| 5,314,409 A | 5/1994 | Sarosiek et al. |
| 5,389,074 A | 2/1995 | Parker et al. |
| 5,549,626 A | 8/1996 | Miller et al. |
| 5,827,324 A | 10/1998 | Cassell et al. |
| 6,302,917 B1 | 10/2001 | Dua et al. |
| 6,723,053 B2 | 4/2004 | Ackerman et al. |
| 6,958,052 B1 | 10/2005 | Charlton |
| 7,013,899 B2 | 3/2006 | Alfery et al. |
| 7,040,322 B2 | 5/2006 | Fortuna |
| 7,140,370 B2 | 11/2006 | Tresnak et al. |
| 7,761,169 B2 | 7/2010 | Zelickson et al. |
| 7,762,261 B1 | 7/2010 | Fortuna |
| 7,887,560 B2 | 2/2011 | Kusleika |
| 7,942,892 B2 | 5/2011 | D'Aquanni et al. |
| 7,992,565 B2 | 8/2011 | McGuckin, Jr. et al. |
| 2001/0050086 A1 | 12/2001 | Addington et al. |
| 2003/0028075 A1 | 2/2003 | Ulmsten et al. |
| 2004/0181161 A1* | 9/2004 | Addington et al. ........... 600/529 |
| 2005/0065450 A1* | 3/2005 | Stuebe et al. ................. 600/547 |
| 2005/0265978 A1* | 12/2005 | Chancellor et al. ........ 424/93.7 |
| 2005/0288603 A1* | 12/2005 | Goping ......................... 600/561 |
| 2007/0027549 A1 | 2/2007 | Godin |
| 2007/0123793 A1 | 5/2007 | Addington et al. |
| 2007/0135736 A1 | 6/2007 | Addington et al. |
| 2007/0185371 A1* | 8/2007 | Bortolotti ...................... 600/29 |
| 2007/0225576 A1* | 9/2007 | Brown et al. ................. 600/301 |
| 2007/0255090 A1 | 11/2007 | Addington et al. |
| 2008/0039786 A1 | 2/2008 | Epstein et al. |
| 2008/0065008 A1 | 3/2008 | Barbut et al. |
| 2008/0077043 A1* | 3/2008 | Malbrain et al. .............. 600/547 |
| 2009/0012350 A1* | 1/2009 | Tihon ............................... 600/30 |
| 2009/0018498 A1 | 1/2009 | Chiu et al. |
| 2009/0062771 A1 | 3/2009 | Tarola et al. |
| 2009/0124937 A1* | 5/2009 | Parks .......................... 600/593 |
| 2010/0010532 A1 | 1/2010 | Vallabhaneni |
| 2010/0076254 A1* | 3/2010 | Jimenez et al. ................. 600/30 |
| 2010/0137736 A1 | 6/2010 | Addington et al. |
| 2010/0137737 A1 | 6/2010 | Addington et al. |
| 2010/0163023 A1 | 7/2010 | Singh |
| 2010/0224186 A1 | 9/2010 | Uesugi |
| 2011/0040157 A1 | 2/2011 | Addington et al. |
| 2011/0040211 A1 | 2/2011 | Addington et al. |
| 2011/0046653 A1 | 2/2011 | Addington et al. |
| 2011/0054272 A1* | 3/2011 | Derchak ....................... 600/301 |
| 2011/0060215 A1* | 3/2011 | Tupin et al. ................... 600/425 |
| 2011/0066175 A1 | 3/2011 | Gross |
| 2011/0166556 A1 | 7/2011 | Shalon |
| 2012/0041465 A1 | 2/2012 | Shalon |
| 2012/0190938 A1 | 7/2012 | Addington et al. |
| 2012/0277547 A1 | 11/2012 | Addington et al. |
| 2012/0277583 A1 | 11/2012 | Addington et al. |
| 2013/0012920 A1 | 1/2013 | Elia et al. |

FOREIGN PATENT DOCUMENTS

| | | | |
|---|---|---|---|
| WO | 2004/073516 | 9/2004 | |
| WO | WO 2007079271 A2 * | 7/2007 | ............... A61B 5/03 |
| WO | WO 2007081626 A2 * | 7/2007 | ............... A61B 5/07 |
| WO | 2009141598 | 11/2009 | |
| WO | 2012100170 | 7/2012 | |

* cited by examiner

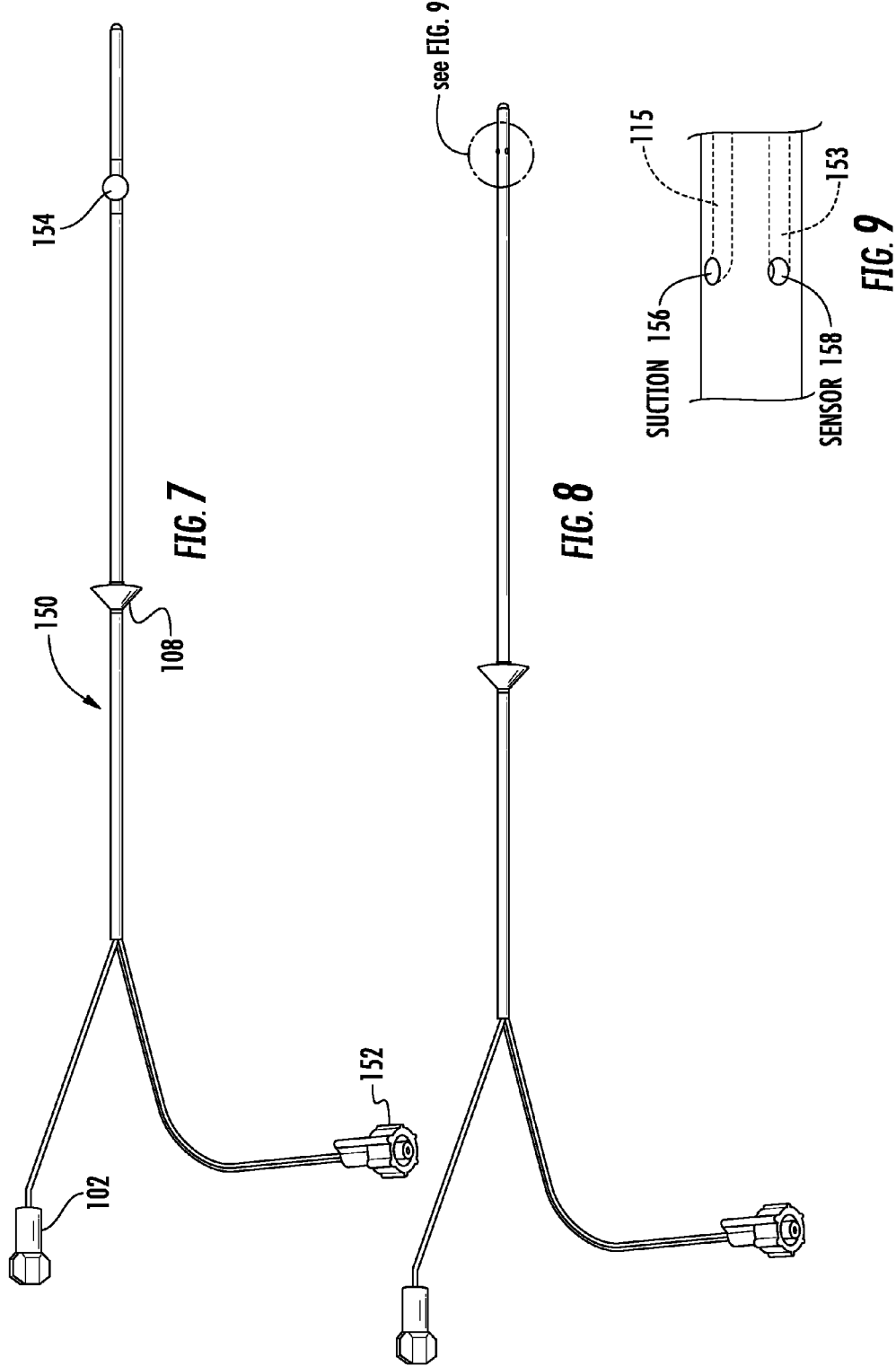

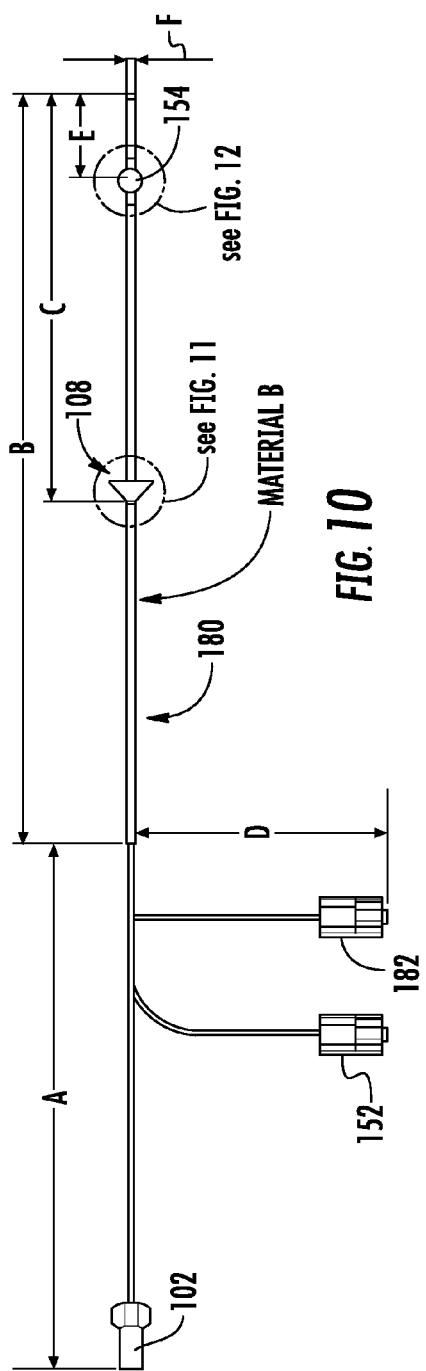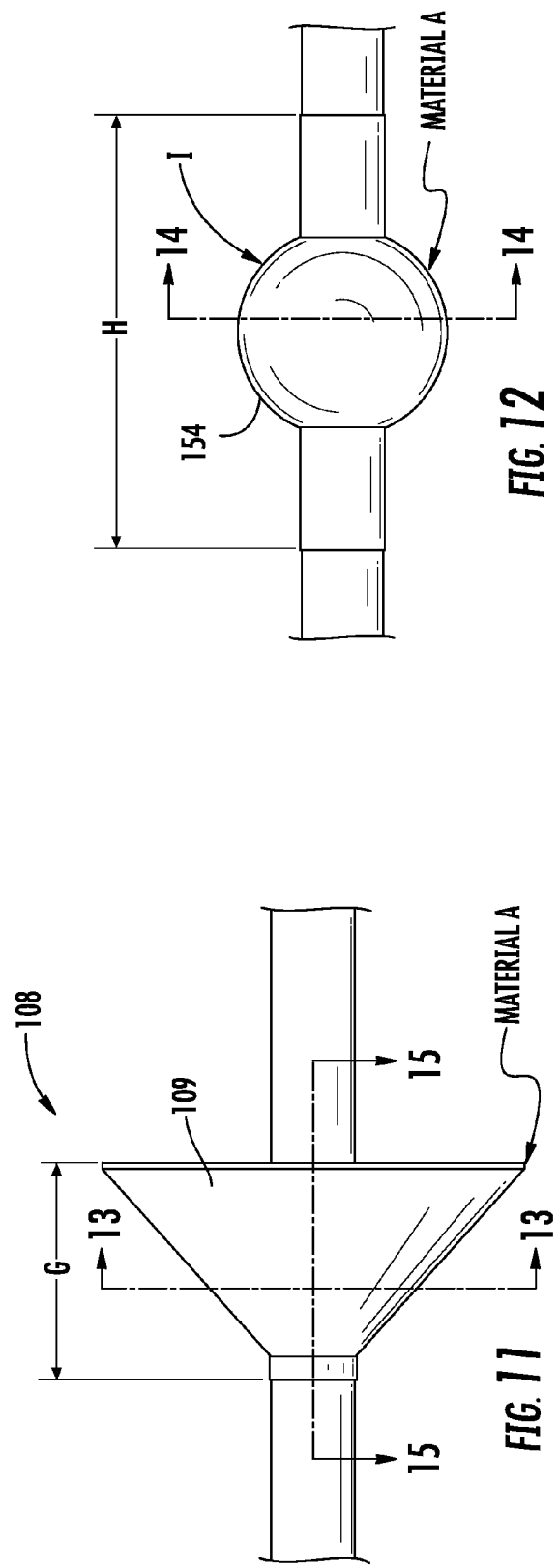

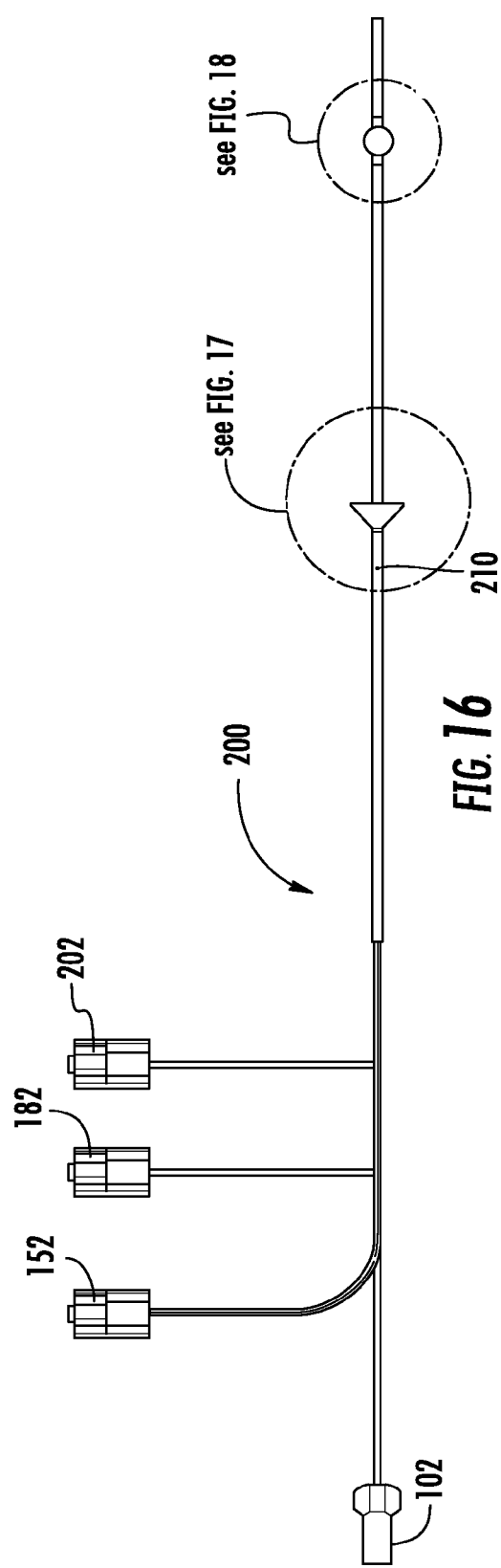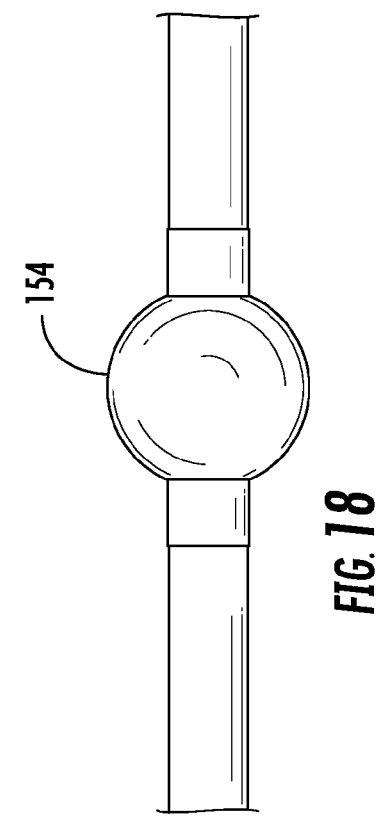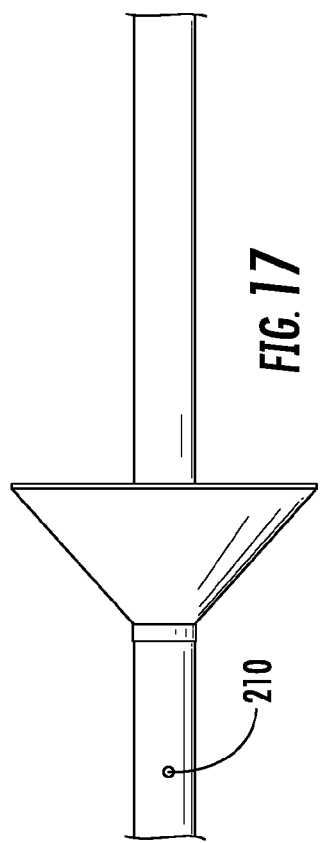

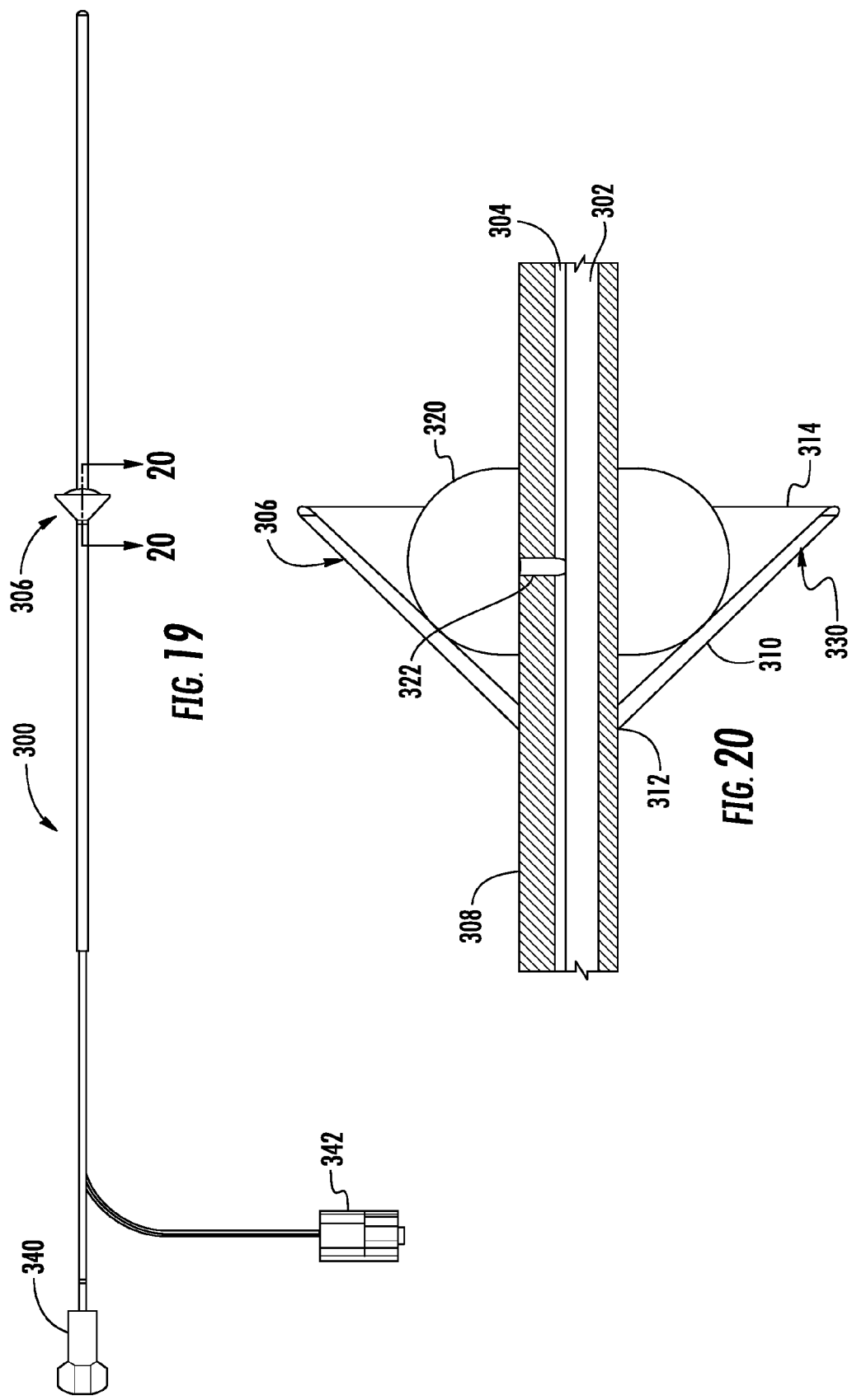

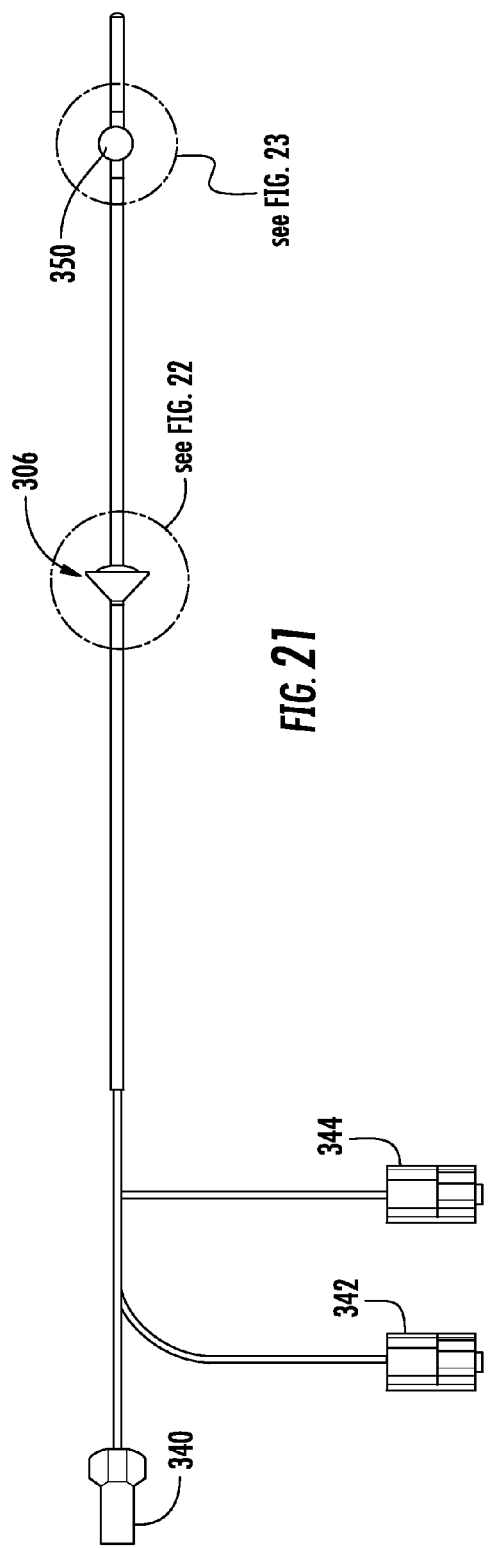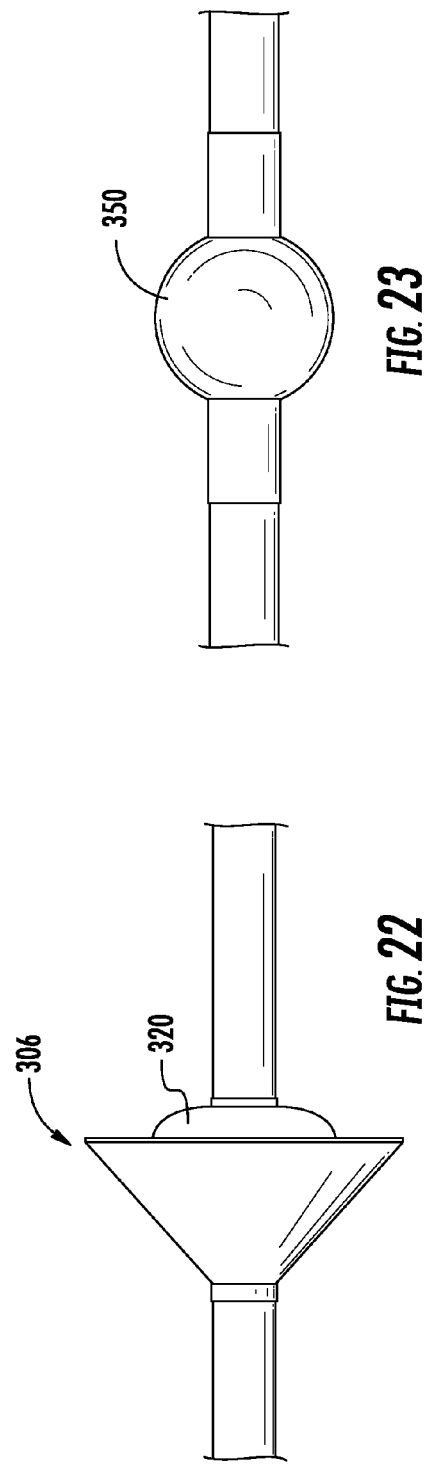

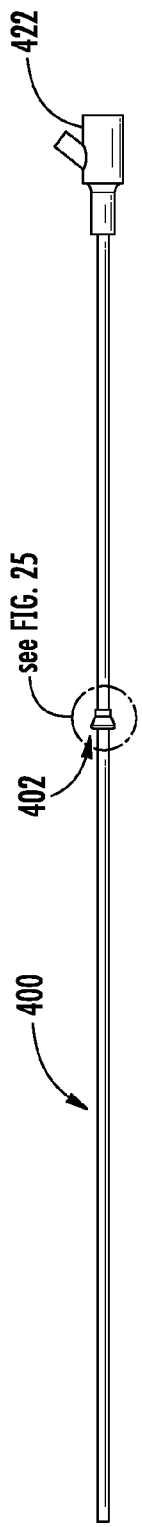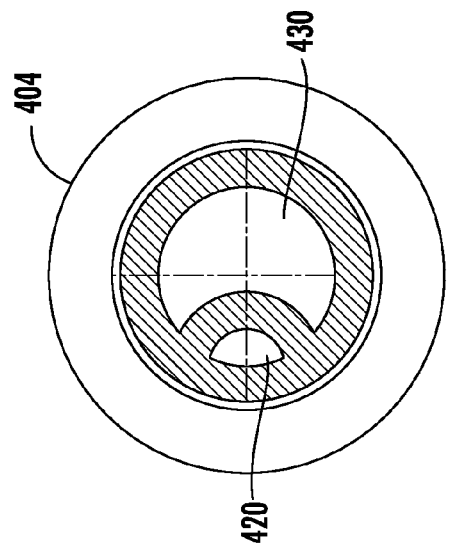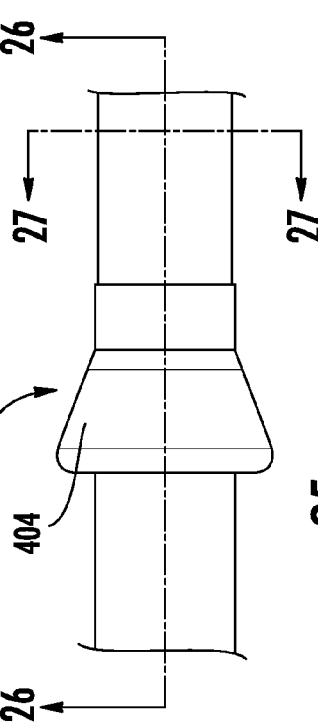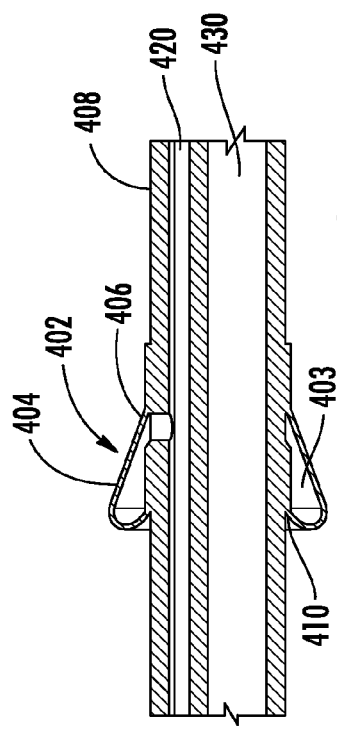
FIG. 24
FIG. 25
FIG. 26
FIG. 27

DEVICE WITH PASSIVE VALVE TO BLOCK EMESIS AND/OR REFLUX AND ASSOCIATED SYSTEM AND METHOD

FIELD OF THE INVENTION

This invention is related to the field of medical devices, and more particularly, this invention is related to a device for blocking emesis and/or reflux and a system of diagnosing a physiological abnormality in a patient by inducing an involuntary reflex cough test (iRCT).

BACKGROUND OF THE INVENTION

Commonly assigned U.S. application Ser. No. 13/354,100 filed Jan. 19, 2012 by the same inventors, the disclosure which is hereby incorporated by reference in its entirety, discloses a system and method of diagnosing acid reflux using an involuntary reflex cough test. In one example as disclosed, a nasogastric/orogastric (Ng/Og) device is inserted though the mouth or nose and through the esophagus and into the stomach and the involuntary reflex cough epoch induced. The intra-abdominal pressure and elevational reflux along the Ng/Og device is measured. In an example, the functional status of the gastric valve is determined based on the measured intra-abdominal pressure and elevational reflux along the catheter. This procedure is sometimes a limited analysis that is not always accurate to determine whether there is a reflux problem, and thus, requiring an Ng/Og device, which in some cases can interfere with the gastric valve and the lower esophageal sphincter. In another example, an Ng/Og device with an esophageal cuff is used. A sequence of steps occur, e.g., inflating the esophageal cuff, inducing the involuntary reflex cough epoch, determining if acid reflux has occurred, deflating the esophageal cuff, and again inducing the involuntary reflex cough epoch. Results are analyzed to determine the functional status of the gastric valve.

Use of the involuntary reflex cough test with or without a voluntary cough test is also disclosed in commonly assigned U.S. patent application Ser. No. 11/608,316 filed Dec. 8, 2006; Ser. No. 11/550,125 filed Oct. 17, 2006; Ser. No. 12/643,134 filed Dec. 21, 2009; Ser. No. 12/643,251 filed Dec. 21, 2009; Ser. No. 12/878,257 filed Sep. 9, 2010; Ser. No. 12/878,281 filed Sep. 9, 2010; and Ser. No. 12/878,316 filed Sep. 9, 2010; the disclosures which are all hereby incorporated by reference in their entirety. The '257, '281 and '316 applications disclose nasogastric/orogastric (Ng/Og) devices, some with or without esophageal cuffs and/or reflux measurement systems that can be used to assess GERD or determine stress urinary incontinence or other physiological abnormalities using the involuntary reflex cough tests alone or in combination with the voluntary cough test.

These applications also disclose summary results when the involuntary reflex cough test is induced. In one embodiment, a handheld or other processing device processes the test results. Various urinary bladder catheters are also disclosed that may include various indicators. In another example, the Ng/Og device includes an esophageal cuff carried by the device and positioned in the esophagus to reduce or diminish gastric reflux and/or emesis in surgical, neurological and/or trauma patients. These applications also disclose further developments regarding use of the involuntary reflex cough test.

Commonly assigned U.S. patent application Ser. Nos. 13/456,841 and 13/456,882, the disclosures which are hereby incorporated by reference in their entirety, disclose systems and methods that test the gastric valve and urethral sphincter. A contrast agent is administered into the esophagus of a patient followed by inducing an involuntary reflex cough epoch to isolate the gastric valve from the Lower Esophageal Sphincter (LES). In an example, it is possible to isolate the external urethral sphincter from the internal urethral sphincter. An imaging sensor detects the flow of the contrast agent during the involuntary reflex cough epoch and determines whether stomach reflux occurred indicative of a malfunctioning gastric valve. A determination may be made if urine leakage occurs indicative of Stress Urinary Incontinence (SUI). In these types of tests an emesis and reflux blocking can be important and improved devices that block emesis and/or reflux and during the involuntary reflex cough test are desirable.

SUMMARY OF THE INVENTION

A device to block emesis and/or reflux includes a tube insertable into the esophagus. A valve is carried by the tube and includes a flexible sheath having an upper edge secured onto the tube and an unsecured lower circumferential edge and configured such that upon contact with emesis and/or reflux from the stomach, the flexible sheath opens in a concave configuration towards the stomach and the unsecured lower circumferential edge engages the esophageal wall and blocks emesis and/or reflux from the stomach passing into the esophagus past the valve.

The tube has a distal end and a proximal end and is configured for insertion through a patient's esophagus such that the distal end is received within the patient's stomach. A sump lumen extends the length of the tube and a sump port at the distal end of the tube communicates with the sump lumen and is configured to vent gas. In another example, the valve is positioned on the tube to be mid-esophagus below the aortic notch when the tube is received through the esophagus. A radio-opaque marker is carried by the valve to aid in positioning the valve mid-esophagus. In another example, the valve is configured to be positioned at about 2 to about 3 cm below the aortic notch when the tube is received through the esophagus.

In another example, a securement engages and secures the flexible sheath into a closed configuration. Upon insertion of the tube within the patient's esophagus, the securement is released allowing the flexible sheath to open freely. In one example, the securement is water soluble and in another example, the securement comprises a sliding ring member.

In another example, the flexible sheath is formed from a multiple density flexible material with the closed position as a normal state. The material forming the unsecured lower circumferential edge is formed to minimize damage to the esophageal wall as it makes contact therewith. The flexible sheath may be formed to open in the concave formation upon a predetermined pressure of emesis and/or reflux from the stomach. The tube is formed of multiple lumens including a lumen for suction in another example. At least one pressure sensor may be carried by the tube.

A system for diagnosing a physiological abnormality in a patient is disclosed. A tube is insertable into the esophagus. A valve is carried by the tube and includes a flexible sheath having an upper edge secured onto the tube and an unsecured lower circumferential edge and configured such that upon contact with emesis and/or reflux from the stomach, the flexible sheath opens in a concave configuration towards the stomach. The unsecured lower circumferential edge engages the esophageal wall and blocks emesis and/or reflux from the stomach passing into the esophagus past the valve to protect a patient's airway during an involuntary reflex cough event. At least one sensor senses a physiological condition of the patient during the involuntary reflex cough event. A processing device is connected to the at least one sensor and configured to process the sensed physiological condition that occurs during the involuntary reflex cough event to determine a physiological abnormality.

In another example, the at least one sensor includes a pressure sensor carried by the tube and configured to measure intra-abdominal pressure (IAP). An electromyogram (EMG) pad is configured to obtain an EMG from the involuntary cough activated paraspinal muscles. The processing device is configured to receive the IAP and EMG and correlate the IAP and EMG with the involuntary reflex cough event to determine a physiological abnormality. A second pressure sensor is carried by the tube and the processing device correlates sensed pressure from the second pressure sensor with the IAP and EMG. A pH sensor may be carried by the tube and the processing device correlates pH measurements from the pH sensor with the IAP and EMG.

In another example, the processing device includes a portable handheld device and at least one interface to receive measurements from the at least one sensor obtained during the involuntary reflex cough event. A processor is carried by the housing and configured to receive the measurements from the at least one sensor obtained during the involuntary reflex cough event. A method aspect is also disclosed.

BRIEF DESCRIPTION OF THE DRAWINGS

Other objects, features and advantages of the present invention will become apparent from the detailed description of the invention which follows, when considered in light of the accompanying drawings in which:

FIG. 7 is a fragmentary plan view of a dual lumen device similar to the single lumen device shown in FIG. 3 and showing a balloon positioned at the distal end.

FIG. 8 is another fragmentary plan view of the dual lumen device similar to that shown in FIG. 7 and showing a sensor at the distal end.

FIG. 9 is an enlarged plan view of the distal end of the device in FIG. 8 and showing a suction port and sensor.

FIG. 10 is a fragmentary plan view of a triple lumen device showing an opened passive valve and a balloon positioned at the distal end in accordance with a non-limiting example.

FIG. 11 is an enlarged plan view of the opened passive valve shown in FIG. 10.

FIG. 12 is an enlarged plain view of the balloon shown in FIG. 10.

FIG. 16 is a fragmentary plan view of a quad lumen device that may include an additional lumen for suction above the valve or for other purposes.

FIG. 17 is an enlarged plan view of the passive valve shown in FIG. 16.

FIG. 18 is an enlarged plan view of the balloon shown in FIG. 16.

FIG. 19 is a fragmentary plan view of an active emesis containment device having an active valve that includes an inflatable balloon carried by the tube under the flexible sheath to open the valve upon inflation of the balloon in accordance with a non-limiting example.

FIG. 20 is a sectional view of the device taken along line 20-20 of FIG. 19.

FIG. 21 is a fragmentary view of a triple lumen, active device similar to that active device shown in FIG. 19 and showing a balloon at the distal end.

FIG. 22 is an enlarged plan view of the active valve shown in FIG. 21.

FIG. 23 is an enlarged plan view of the balloon shown in FIG. 21.

FIG. 24 is a fragmentary plan view of another embodiment of the device that uses an alternate configuration of an active valve with a different balloon configuration.

FIG. 25 is an enlarged plan view of the active valve shown in FIG. 24.

FIG. 26 is a sectional view of the active valve taken along line 26-26.

FIG. 27 is a sectional view of the active valve taken in the direction of line 27-27 of FIG. 25.

DETAILED DESCRIPTION OF THE PREFERRED EMBODIMENTS

Figure 1:
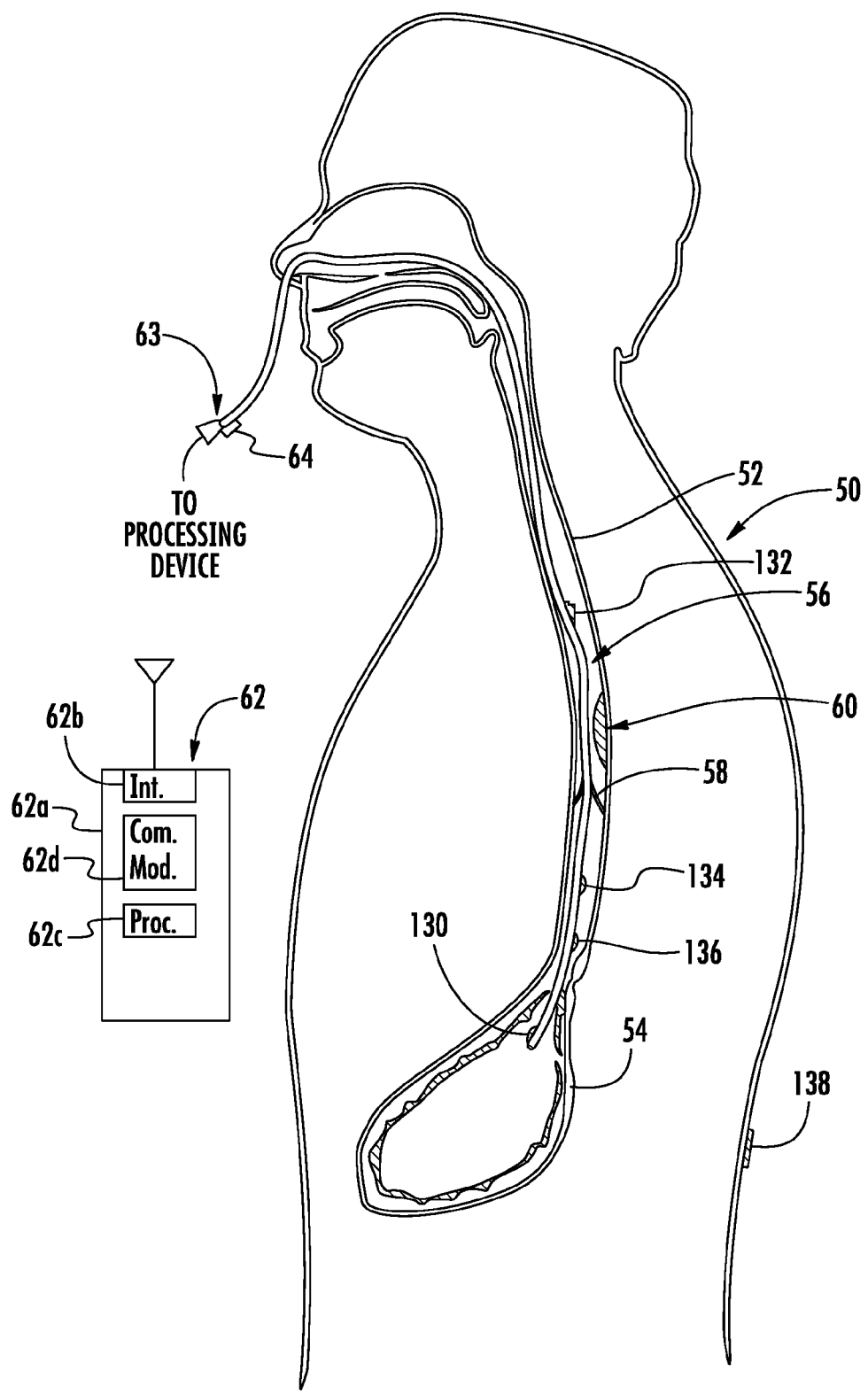
FIG. 1 is a diagrammatic view of a patient and showing the device in accordance with a non-limiting example inserted through the mouth into the esophagus and the valve positioned below the aortic notch.

Different embodiments will now be described more fully hereinafter with reference to the accompanying drawings, in which preferred embodiments are shown. Many different forms can be set forth and described embodiments should not be construed as limited to the embodiments set forth herein. Rather, these embodiments are provided so that this disclosure will be thorough and complete, and will fully convey the scope to those skilled in the art.

As will be described in detail below, FIGS. 2-18 illustrate a passive emesis containment system formed in this example as a nasogastric (Ng) tube having a passive valve and FIGS. 19-27 illustrate an active emesis containment system as a nasogastric (Ng) tube that includes an active valve having an inflatable balloon or other member that actively opens the valve. It should be understood that the tubes could be formed as many different types of nasogastric/osogastric (Ng/Og) tubes depending on the design requirements of those skilled in the art.

The device may include lumens for medication delivery and/or a sump port and sump lumen formed the length of the device body and configured for venting gas and preventing adherence of the device against the gastric wall. In either the passive emesis containment device or the active emesis containment device, a valve is carried by the device body mid-esophagus. During an emesis and/or reflux event, the valve opens such as through the pressure applied by the emesis and/or reflux when a passive valve is used or via a balloon and inflation lumen or other mechanism. Upon expansion of the valve, emesis and/or reflux is blocked from passing out of the stomach and past the valve that is positioned mid-esophagus to protect a patient's airway.

In an example, the passive emesis containment device as shown in FIGS. 2-18 may be formed as a single or multiple lumen tube. A dense material may form the passive valve and a securement may keep the passive valve in a closed position. Pressure such as from emesis and/or reflux may open the passive valve. In another example, the passive valve has a securement that maintains the valve closed. In another example a sliding ring is positioned around the valve. A securement could be water soluble or moveable as in the case of the sliding ring. When the tube is placed in the esophagus, the passive valve would be free to open when emesis pressure is placed against the passive valve or the ring could slide away as the device is inserted into the esophagus to allow the valve to open. The passive valve could be made of multiple density materials with the closed position as the normal resting state. When opened, the passive valve is concave towards the stomach for maximum blocking effectiveness. In an example, the passive valve is formed as a pliable material when in contact with the esophageal wall limiting damage to the wall. The passive valve can be capable of multiple opening pressures such as between about 2 and 30 psi.

The active emesis containment device is shown in FIGS. 21-27. The active valve could be a balloon positioned under the flexible sheath and inflated via an automatic device or inflated manually from a cuff or other mechanism with about 2 to about 3 milliliters (ml) of air or other fluid in one embodiment. The active valve is closed until it is activated and can also be made of multiple density materials as in the passive valve such that the closed position is a normal resting position. The active valve when opened is concave towards the stomach for maximum blocking effectiveness and formed of a multiple density material such that a pliable material is in contact with the esophageal wall, limiting damage to the wall.

Any number of passive or active devices with one or more lumens and different sensors and valve openings are possible. It is possible to have a dual lumen tube with a pressure sensor. In another example, a triple lumen tube has an air pressurized balloon and pressure sensor. A dual lumen tube may include an air pressurized balloon. A quad lumen tube may include a pressurized balloon, TDOC air charged pressure sensor and a suction lumen above the balloon. A single lumen tube may include a balloon that opens in the presence of emesis and/or reflux. The distal balloons may be formed to slide up and down passively. The balloons or valve may be located about 2 to about 3 cm below the aortic notch. Different Ng/Og devices may have radio-opaque markers at the balloon cuff and along the length of the catheter. It is also possible to have a dual lumen tube with passive valve and pressure sensor or triple lumen tube with an active valve and pressure sensor. Another example is a quad lumen tube with suction above the valve or multiple sensors in combination. The valves are placed about 2 to about 3 cm below the aortic notch. Suction ports can be formed as multiple openings in a circumferential pattern. Fill ports may have luer lock fittings.

FIG. 1 is a diagrammatic view of a patient's body 50 and showing the esophagus 52 and stomach 54 of the patient and showing inserted within the esophagus the device 56 used to block emesis and/or reflux in accordance with a non-limiting example. The device is inserted into the esophagus through the mouth and with the valve 58 positioned below the aortic notch 60. The distal end of the tube is insertable through the esophagus and into the stomach as illustrated. FIG. 1 shows the device formed as a nasogastric (Ng) device, but the device could be formed a nasogastric/orogastric (Ng/Og) device and inserted through the mouth or notes. The device could be formed as a single, double, triple or quad or other multiple lumen tube. Depending on design, the device preferably carries at least one sensor that such as a pressure sensor at the distal end communicates to a processing device 62 either through a connecting wire or a wireless connection such as Bluetooth or other RF connection. The proximal end 63 of the tube could include a wired connection to transmit data signals from any device sensors to the processing device 62 or a transmitter module 64 for wireless communication of data signals from any device sensors as illustrated. FIG. 1 is illustrated to show the relative position of the valve about 2 or about 3 centimeters (cm) below the aortic notch. The valves can be passive or active and could use a balloon in the case of an active valve. Reference is made to the incorporated by reference '257, '281 and '316 applications disclosed above that discuss valve placement positions and mechanisms that can be used in conjunction with Ng/Og devices.

Figure 2:
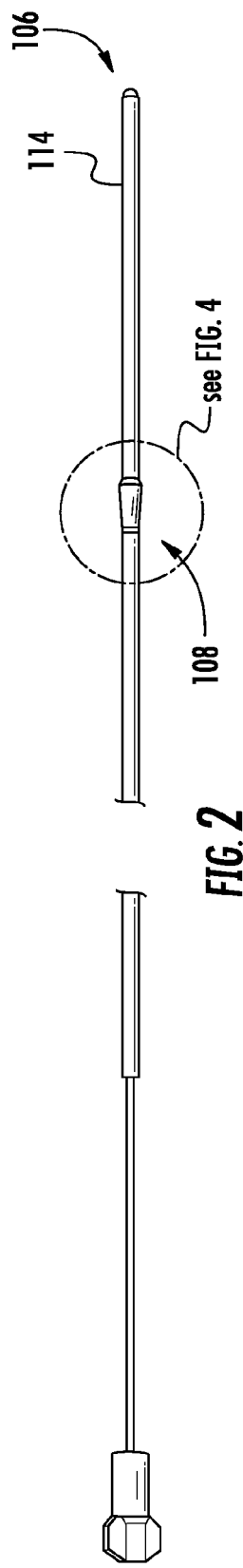
FIG. 2 is a fragmentary plan view of a single lumen passive device in accordance with a non-limiting example and showing a passive valve in a closed position.
Figure 3:
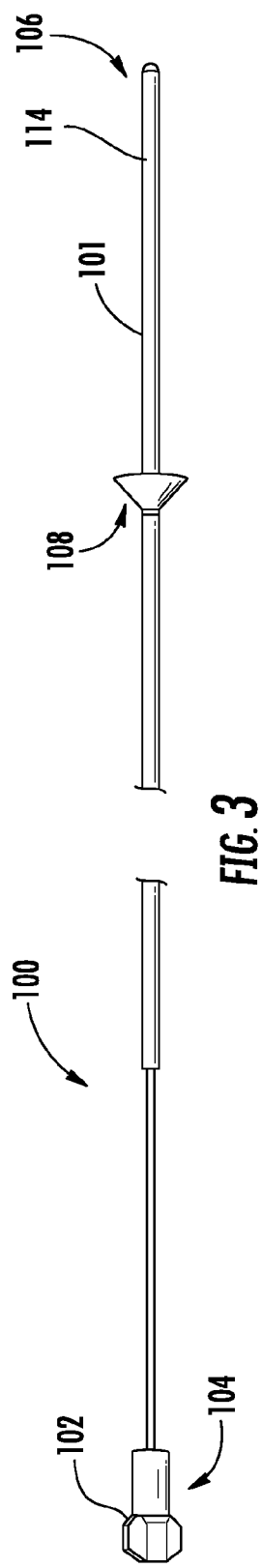
FIG. 3 is a fragmentary plan view of the device shown in FIG. 2 and showing the passive valve in an open position.
Figure 5:
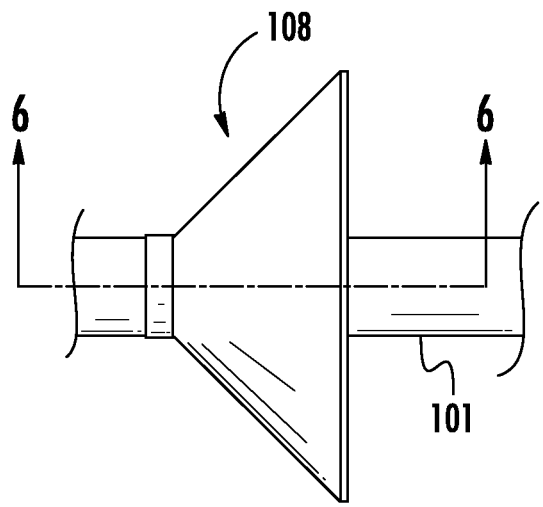
FIG. 5 is a plan view of the passive valve shown in FIG. 3 and in an opened configuration.
Figure 6:
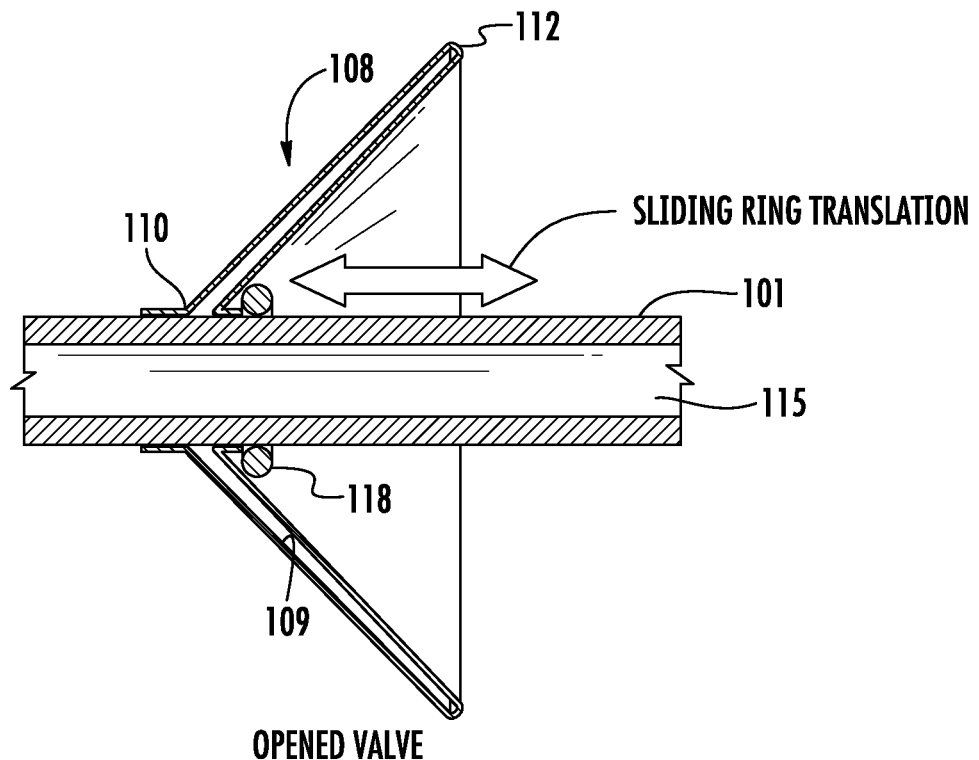
FIG. 6 is an enlarged sectional view taken along line 6-6 of FIG. 5 and showing a sliding ring that may be used as a securement in accordance with a non-limiting example.

FIG. 2 is a fragmentary plan view of a single lumen passive device 100 formed as a tube 101 that shows a luer lock 102 at the proximal end 104 and a distal end 106 and a passive valve 108 carried by the tube and comprising a flexible sheath having an upper edge 110 (FIG. 6) secured onto the tube 101. The upper edge is preferably circumferential in configuration as illustrated and secured to the tube along its entire edge. An unsecured lower circumferential edge 112 is configured such that upon contact of the sheath 109 with emesis and/or reflux from the stomach, the flexible sheath opens in a concave configuration as shown in FIGS. 5 and 6 towards the stomach. When the valve 108 is open, the lower circumferential edge 112 engages the esophageal wall and blocks emesis and/or reflux from the stomach passing into the esophagus and past the valve 108 as shown in FIG. 1. A suction opening 114 is positioned at the distal end and received within the patient's stomach as illustrated in FIG. 1. The tube 101 may define a single lumen 115 (FIG. 6) or as sump lumen that extends the length of the tube and the suction opening may define a sump port at the distal end of the tube and configured to vent gas. The suction opening could be at the very distal end of the tube.

As shown in FIG. 1, the valve 108 is positioned on the tube to be positioned mid-esophagus about 2 to about 3 cm below the aortic notch. A radio-opaque marker 116 is positioned on the valve 108 or adjacent thereto to aid a clinician or physician to position the valve mid-esophagus about two or about three centimeters (cm) below the aortic notch. For example, a clinician or physician may observe the travel of the valve 108 using its radio-opaque marker 116 as it descends the esophagus so that it can be positioned below the aortic notch.

Figure 4:
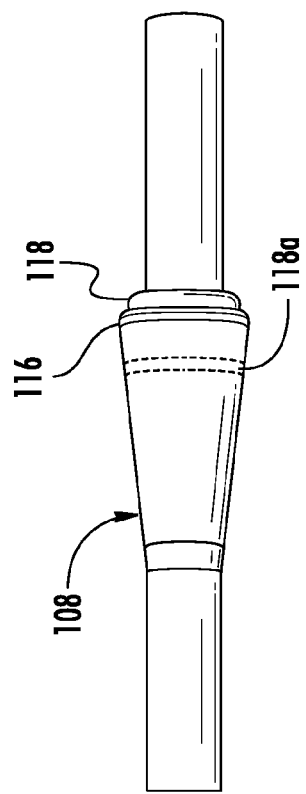
FIG. 4 is an enlarged plan view of the passive valve and showing a securement maintaining the passive valve in a closed position in accordance with a non-limiting example.

FIG. 4 shows a securement 118 such as a ring that engages and secures the flexible sheath in its closed or confined configuration shown in FIGS. 2 and 4. In one example, upon insertion of the tube within the patient's esophagus, this ring or securement 118 is released to allow the valve to open. In the case of a ring as shown in FIG. 4, emesis from the stomach may exert pressure onto the ring and slide it upward to open the valve as shown in FIG. 6. The securement could also be formed of a water soluble material similar to a band around the closed valve as shown in FIG. 4 at 118*a*. This water soluble band 118*a* is dissolved when the valve enters the esophagus to allow the flexible sheath to open freely when emesis presses upward. In each example, the sheath open freely when esophageal pressure is exerted against the valve and it opens in a concave formation. It can be configured to open when a predetermined pressure of emesis and/or reflux extends upward from the stomach. In an example, the amount of emesis and/or reflux pressure that opens the passive valve varies, but in a non-limiting example, the valve is formed to open from about 2 psi to about 30 psi. The passive valve can be designed to open at selected pressures depending on the design configuration, the type of material forming the valve, and the amount of esophageal pressure exerted against the valve. The passive valve can be designed to open at a preselected pressure or range of pressure depending upon the sex, age, general health or medical conditions or other details of the patient. In one example, the flexible sheath 109 is formed from a multiple density flexible material with the closed position of the valve as a normal state and the material forming an unsecured lower circumferential edge 112 formed to minimize damage to the esophageal wall as it makes contact therewith.

FIG. 1 also illustrates a system for diagnosing a physiological abnormality in a patient. The valve is free to open in a concave configuration towards the stomach as shown in FIG. 1 and the unsecured lower circumferential edge 112 will engage the esophageal wall and block emesis and/or reflux from the stomach passing into the esophagus past the valve to protect the patient's airway if any emesis and/or reflux occurs into the esophagus during an involuntary reflex cough event. Greater details of the involuntary reflex cough test as an event and its physiology are explained in the incorporated by reference '257, '281 and '316 applications.

As shown in FIG. 1, the processing device 62 is connected in the example wirelessly through the transmitter module 64 at the device proximal end 63 to at least one sensor and configured to process the sensed physiological condition that occurs during the involuntary reflex cough event and process that data and determine a physiological abnormality. A sensor in one example could include a first pressure sensor 130 at the distal end of the tube that is received with the patient's stomach. A second pressure sensor 132 and third pressure sensor 134 are positioned above and/or below the aortic notch 60 or above and/or below the valve 58. A pH sensor 136 is included as illustrated. A pH sensor 136 may be located at a selected area along the tube as explained in the various incorporated by reference patents. Multiple pH sensors may also be used. An electromyogram (EMG) pad 138 is configured to obtain an EMG from involuntary cough activated paraspinal muscles. The processing device is configured to receive the IAP and EMG and correlate the IAP and EMG with the involuntary reflex cough event and determine a physiological abnormality. In another example, the processing device 62 correlates pressure from the second pressure sensor 132 with the IAP and EMG. The processing device also may correlate pH measurements from the pH sensor 136 with the IAP and EMG. Multiple pH sensors may be positioned along the tube and data from each sensor corrected. Further details of the involuntary reflex cough event and data processing are set forth in the incorporated by reference '257, '281 and '316 applications.

In one example, the processing device 62 is formed as a portable handheld device as shown and explained in greater detail in the '257, '281 and '316 applications and includes a housing 62*a* at least one interface 62*b* to receive measurements from at least one sensor such as a pressure sensor and/or EMG pad obtained during the involuntary reflex cough event. A processor 62*c* is carried by the housing and operative with a communications module 62*d* and configured to receive through the interface 62*b* the data measurements from different sensors obtained during the involuntary reflex cough event. In a system shown in FIG. 1, a nebulized medication is administered to the patient to activate the involuntary reflex cough event. This nebulized medication could be administered such as through a nebulizer lumen formed in the device or using a standard nebulizer.

FIGS. 7-9 show a dual lumen device 150 that includes the first luer lock 102 for a first lumen 115 and a second luer lock 152 for a second lumen 153, the valve 108 and a balloon 154 on the distal end that could operate as a sensor or a placement device. In the example of FIGS. 8 and 9, a first lumen is provided for suction 156 and a second lumen for a sensor 158 as shown in FIG. 9. The balloon 154 in FIG. 7 could operate a sensor or be used for positioning, securement or other physiological mechanisms. As described below, different embodiments could be used.

FIGS. 10-15 show a triple lumen passive device 180 with a third luer lock 182 and a balloon 154 as in FIG. 7. FIG. 10 shows relative dimensions of various components and illustrates how the valve 108 could be made from different density materials. It should be understood that the material description and described dimensions may apply to any of the devices whether passive or active as shown in all the figures. For example, material A as shown in FIG. 11 corresponds to the portion of the sheath material that engages the esophagus when the valve is opened and could be formed from a material such as "nylon 12" and be about 0.02 inches thick in a non-limiting example. Material B for the tube material shown in the example of FIG. 10 could be formed from PET (polyethylene terephthalate). It should be understood that other similar materials could be used as selected by those skilled in the art. FIG. 11 is an enlarged view of the passive valve shown in FIG. 10 and FIG. 12 is an enlarged view of the balloon shown in FIG. 10. The sectional view taken along line 13-13 in FIG. 11 shows the flexible sheath 109 and a central or first lumen 115 for suction or a sump lumen and a second lumen 153 and third lumen 184 that are smaller in diameter and used for a variety of purposes, for example, two sensors, a sensor and balloon or other function. The sectional view taken along line 15-15 of FIG. 11 shows the larger first lumen 115 and second lumen 153 such as for a sensor and third lumen 184 for a balloon, for example.

Figure 13:
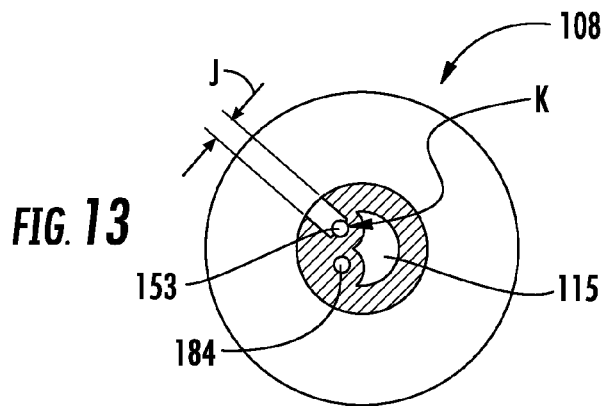
FIG. 13 is a partial sectional view taken along line 13-13 of FIG. 11.
Figure 14:
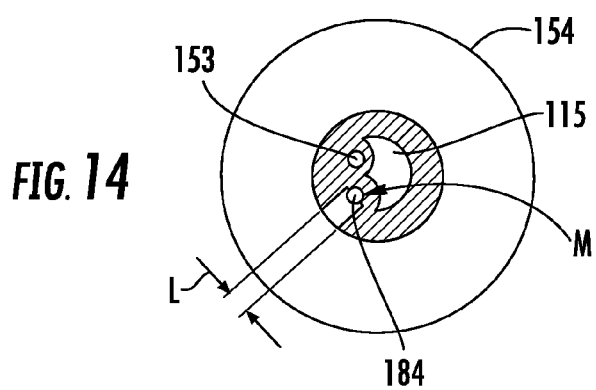
FIG. 14 is a sectional view taken along line 14-14 of FIG. 12.
Figure 15:
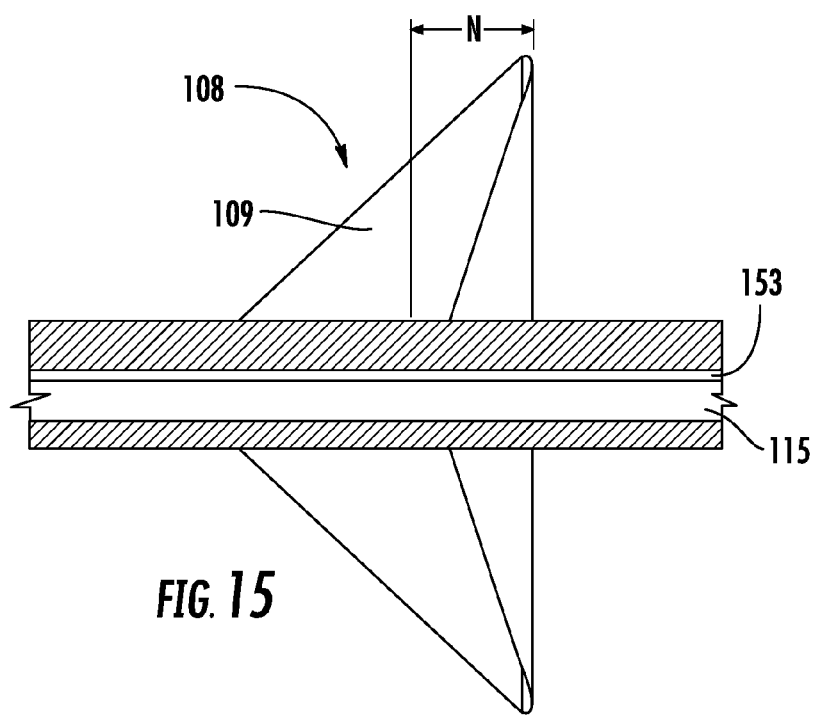
FIG. 15 is a sectional view taken along line 15-15 of FIG. 11.

Representative non-limiting examples of the device are now set forth with reference to FIGS. 10-15, but as noted before, can apply to other figures. Referring to FIG. 10, dimension A is 20 inches in a non-limiting example and dimension B is 54.6 inches. Dimension C is 30 inches and dimension D is 20 inches for each luer lock tube in this particular example. Dimension E is 2.54 inches and dimension F is 0.246 inches. These dimensions are non-limiting examples and can vary depending on design requirements for a device as required by those skilled in the art. In FIG. 11, dimension G is 0.666 inches in a non-limiting example. In FIG. 12, dimension H is 1.334 inches and the radius for dimension I in a non-limiting example is 0.318 inches. Referring now to FIG. 13, an example dimension J is 0.050 inches and an example dimension for the radius K is 0.015 inches. As shown in FIG. 14 as a non-limiting example, dimension L is 0.050 inches and dimension M is a radius of 0.015 inches. Dimension N in FIG. 15 is about 0.243 inches and shows a folded inward edge secured on the tube to impart strength to the valve and inhibit upward movement of emesis.

FIGS. 16-18 show a quad lumen device 200 with a fourth luer lock 202 and fourth lumen where FIG. 17 is an enlarged plan view of the passive valve 108 and showing an upper suction hole 210 that connects to the fourth lumen and allows upper secretions in the esophagus that are above the valve to be sucked into a fourth or other lumen and out of the device. In this example the device includes a distal balloon 154 as shown in FIG. 18 similar to previous embodiment distal balloons. This particular embodiment shown in FIGS. 16-18 could include a pressure sensor as part of the distal balloon 154 and/or suction below the valve and/or suction above the valve. Stomach suction may occur through the standard first or main lumen in this example as a sump port in another example.

FIGS. 19 and 20 shows an embodiment of an active device 300 as a dual lumen active device with the first lumen 302 for suction and the second lumen 304 used as an inflation lumen (FIG. 20). The valve is formed as an active valve 306 and is carried by the tube 308 and includes a flexible sheath 310 having its upper circumferential edge 312 secured to the tube and an unsecured lower circumferential edge 314 as in other examples. An inflatable balloon 320 is carried by the tube 308 under the flexible sheath 310 and in communication with the inflation lumen 304 through a lumen side opening 322. Upon inflation of the balloon, the flexible sheath 306 opens in a concave configuration towards the stomach as in previous examples described above and the unsecured lower circumferential edge 314 engages the esophageal wall and blocks emesis and/or reflux from the stomach passing into the esophagus past the valve. The flexible sheath is formed to close when the balloon is deflated. This active device also includes a radio-opaque marker 330 carried by the valve similar to that shown in previous embodiments to aid in positioning the valve mid-esophagus and preferably about 2 to about 3 cm below the aortic notch when the tube is received through the esophagus. As in previous examples, a sump lumen as the first central lumen 302 may extend the length of the tube and a sump port at the distal end of the tube communicates with the sump lumen and is configured to vent gas. The flexible sheath 306 in this example also may be formed from a multiple density flexible material with the closed position as a normal state when the balloon is deflated and the material forming the unsecured lower circumferential edge is formed to minimize damage to the esophageal wall as it makes contact therewith. Typically, after insertion the balloon may be inflated. The sheath could be formed to open in a concave formation such as when a predetermined pressure of emesis and/or reflux from the stomach is sensed and triggers air to be pumped into the inflation lumen and inflate the balloon to expand the sheath. The lumen 302, 304 could connect to first and second luer locks 340, 342.

Pressure could be sensed by a balloon 350 such as shown in FIGS. 21-23 that would measure pressure and in some instances be indicative of emesis and/or reflux and in these examples, the device can be used to diagnose a physiological abnormality by the involuntary reflex cough event. The third luer lock 344 is illustrated as connected to a third lumen.

FIGS. 24-27 illustrate another embodiment of an active device 400 having an active valve 402 in which the balloon 403 is formed as part of the flexible sheath 404 and includes the upper edge 406 secured on the tube 408 and a lower peripheral portion is folded back and an edge 410 is secured on the tube to form the balloon. The inflation lumen receives compressed air to expand outward the sheath and form the valve. The inflatable balloon is formed by the sheath itself in this non-limiting example. The inflation lumen is shown in the sectional view of FIG. 27. Although only one luer lock 442 is illustrated, multiple luer locks could be connected to any second and third lumens. Two lumens are shown in the sectional view of FIG. 26 with the central lumen 430 operative and functionally similar to the central lumens in the other embodiment.

Figure 28:
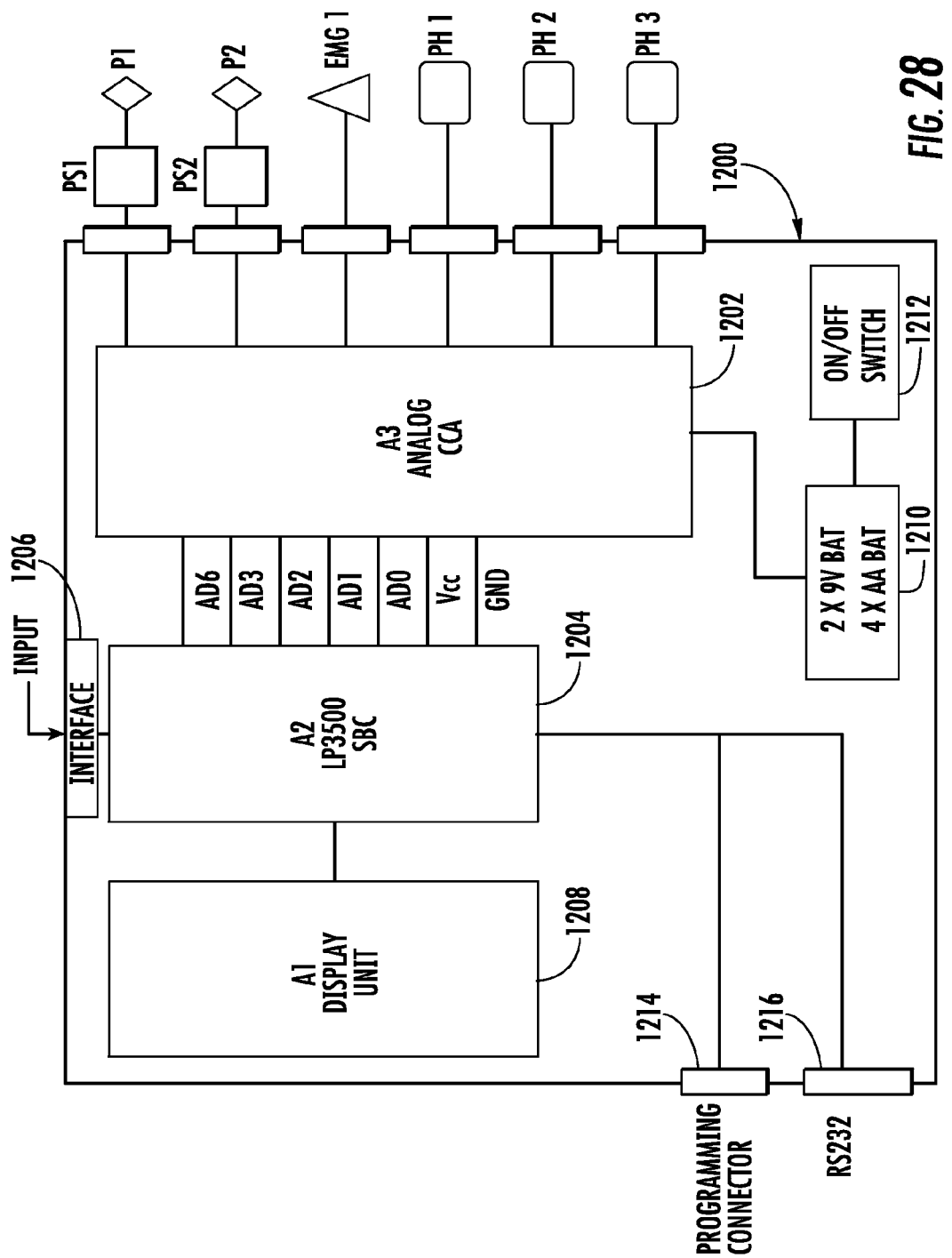
FIGS. 28 and 29 show an example six-channel system for a processing device such as a portable handheld device, including a schematic circuit diagram in FIG. 29 and block diagram in FIG. 28.
Figure 29:
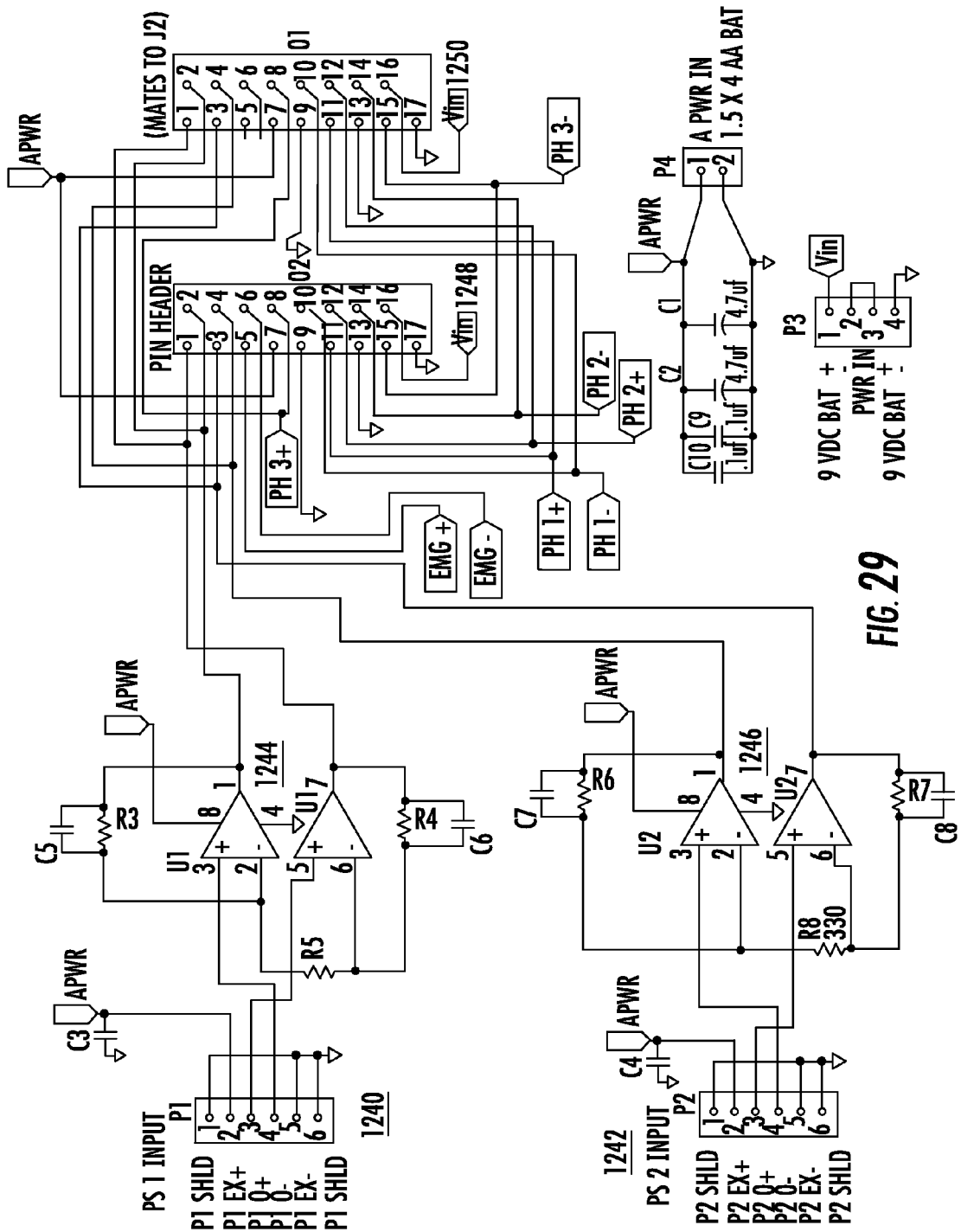

FIGS. 28 and 29 show an example of a six-channel system for a processing device such as the portable handheld device 62 shown in FIG. 1 and including a schematic circuit diagram in FIG. 29 and high-level block diagram in FIG. 2B. Although a six-channel system is shown, it should be understood that a fewer number or greater number of channels can be used depending on the number of sensors and other inputs desired. A portable handheld device and has the processing capability to process numerous inputs besides those shown in FIG. 28 or in the specific device examples of FIGS. 1-27. Data can be transferred with various flow sequences, for example, as explained in FIG. 26-26 and 27-28 in the incorporated by reference '257, '281 and '316 applications.

FIG. 28 is a high-level block diagram of basic components for the handheld device such as shown in FIG. 1 illustrated generally in this example at 1200, which in one non-limiting example, uses wireless technology to receive pressure readings such described in the incorporated by reference '257, '281 and '316 applications. This example relative to FIG. 28 shows a wired connection. In this example for the handheld device 1200, the device includes multiple pressure inputs, for example, to receive Viking connector receptacles and connect to TDOC pressure sensors. As illustrated, the inputs at pressure 1 and pressure 2 correspond to the two respective catheters as inputs through the pressure sensors PS1 and PS2 into a pressure converter circuit 1202, which transmits the pressure signals to the onboard processor 1204 through various AD signal lines as indicated. The pressure converter circuit 1202 includes pressure measurement electronics such as shown in the schematic circuit diagram of FIG. 29 and described in greater detail below. The pressure measurements obtained through the pressure sensors PS1 and PS2 are converted and forwarded to the processor 1204, which in one non-limiting example, is a single board computer such as a Rabbit LP3500. The pressure sensors PS1 and PS2 are in one non-limiting example TDOC-4030 pressure sensors. The catheters used at inputs P1 and P2 correspond in one non-limiting example to TDOC-6F catheters. It should be understood that EMC signals are input through interface circuit 1206 into the processor 1204. Data that is processed is displayed using a display unit 1208 such a display/keyboard/LED, for example a rabbit KDU.

In one non-limiting example, the pressure converter circuit 1202 is powered by two nine-volt batteries or in an alternative embodiment by four AA batteries 1210. The batteries are connected to an on/off switch 1212. A programming connector 1214 and RS232 connector 1216 are connected into the processor 1204 to allow programming of the processor with appropriate software and code as described before and for processing data related to the involuntary reflex cough test. Data can be retrieved or input. This device 1200 accomplishes both SUI and neuroanalysis using the appropriate data analysis.

FIG. 29 is a top plan view of the housing 1220 for the handheld device and showing a location for a power on/off toggle switch 1234 and a display with a keyboard and light emitting diodes (LED's) 1236. Non-limiting examples for possible dimensions for the handheld device are about 8 inches (x) and 5 inches (y).

FIG. 29 is a schematic circuit diagram of the pressure converter 1252 in accordance with a non-limiting example and showing the various pressure sensor 1 input 1240 and pressure sensor 2 input 1242. These are independent channels each with comparators and operational amplifiers illustrated generally at 1244 and 1246 respectively. These components and circuits connect into appropriate pin headers 1248 and 1250 that output to a single board computer in this non-limiting example.

Different processors 1204 as a single board computer can be used in a non-limiting example. The described Rabbit microprocessor is a low-power, single-board computer and is especially operable with portable handheld, battery-powered, remote monitoring systems. It includes built-in analog and digital input/output and typically consumes less than 20 milliamperes when operational and less than 100 microamps in a power-save mode. In this non-limiting example, it includes flash memory and SRAM and various inputs/outputs and in one non-limiting example eight analog/digital converter inputs with programmable gain and six serial ports. It has pulse width modulation (PWM) outputs. It can be programmed using C software in a non-limiting example.

It should be understood that the display unit 1208 as illustrated in FIG. 28 is a separate display unit that includes the display, keyboard and light emitting diodes and supported on the housing, but could be incorporated integral with the single board computer in a non-limiting example.

FIGS. 28 and 29 show a representative six channel system in which three pH inputs are illustrated, for example, for measuring pH, for example, when pH probes or sensors are situated on a device such as shown in FIG. 1 and pH probes or sensors are located in the stomach, at the lower esophageal sphincter (LES), mid-esophageal area, and/or superior esophageal area as a non-limiting example. It should be understood that an eight channel system can also be used in which there may be four pH channels for the four locations as described, two pressure channels and two EMG channels. One of the channels, in the alternative, could be a spare channel. Ten or more channels could be used. Multiple EMG or pressure inputs could be used. The particular choice by channels is a choice of one skilled in the art based on the type of Ng/Og device that is used and what is being analyzed.

In an example, the EMG sensor circuit could incorporate a DELSYS DE-2.1 and the pH measurement probe could incorporate a MediPlus 25100 as non-limiting examples. The pressure sensor could be a TDOC-4030 for PS1 and PS2 and the catheter function as P1 and P2 could be a TDOC-7F.

There now follows an example of a pseudocode, which explains in a more cogent manner the function of the programming code that could be used with the handheld device as described in accordance with a non-limiting example:

```
/*********************************************************************
Function      : Init_Arrays
Description   : Initializes all the arrays to predefined values deemed as having no
valid meaning.
*********************************************************************/
Init_Arrays ( )
    While (index <NUM_ENTRIES)
        VesicularPressure[index]= UNDEF_PRESSURE
        AbdominalPressure [index]= UNDEF_PRESSURE
        DetrusorPressure [index] = UNDEF_PRESSURE
        index = index + 1
    End While
End   // Init_Arrays
/*********************************************************************
Function      : Calculate_Pdet_Array
Description   : Calculates the DetrusorPressure values throughout the cough event and
populates the array accordingly.
*********************************************************************/
Calculate_Pdet_Array ( )
    index = CoughStart
    While (index <=CoughStop)
        DetrusorPressure [index]= VesicularPressure [index] – AbdominalPressure
[index]
        index = index + 1
    End While
End   // Calculate_Pdet_Array
/*********************************************************************
Function      : Normalize_Event_Array
Description   : Normalizes the Pves for the duration of the cough event only, by
subtracting the baseline pressure from every Pves value.
*********************************************************************/
Normalize_Event_Array ( )
    index = CoughStart
    While (index <=CoughStop)
        VesicularPressure [index] = VesicularPressure [index] – BaseLinePressure
        index = index + 1
    End while
End   // Normalize_Event_Array
/*********************************************************************
Function      : Average_ Pressure
Description   : Calculates the average value of an array subset.
*********************************************************************/
Average_Pressure ( )
    Sum = 0;
    index = CoughStart
    While (index <=CoughStop)
        Sum = Sum + VesicularPressure [index]
        index = index + 1
```

```
   End While
   AveragePressure = Sum/ ( CoughStop – CoughStart + 1)
End   // Average_ Pressure
/************************************************************************
Function    : Peak_Pressure
Description : Finds the peak value of an array subset.
************************************************************************/
Peak_Pressure ( )
  PeakPressure = UNDEF_PRESSURE
  index = CoughStart
  While (index <=CoughStop)
    If (VesicularPressure [index] >= PeakPressure)
      PeakPressure = VesicularPressure [index]
    End If
    index = index + 1
  End While
End   // Peak_Pressure
/************************************************************************
Function    : Find_Level_Pressure
Description : Searches a subset of the pressure array for a window where the pressure
is "relatively" level.
************************************************************************/
Find_Level_pressure ( )
  index = 0
  While (index < NUM_ENTRIES)
    Calculate Slope between VesicularPressure [index] and VesicularPressure
[index+1]
    If (Slope < SlopeTolerance)
      If (Duration > XTime) )
        Stop = index−1
        Escape While
      End If
    End if
    index = index + 1
  End While
End   // Find_Level_Pressure
/************************************************************************
Function    : Event_Start
Description : Determines the start point for a cough event by examining the slope
between consecutive points.
************************************************************************/
Event_Start ( )
  index = 0
   While (index < NUM_ENTRIES)
    Calculate Slope between VesicularPressure [index] and VesicularPressure
[index+1]
    If (Slope > SlopeTolerance)
      If (Count > ConsecutiveTimes)
           Start = index
         Escape While
      End If
      Count = Count + 1
    End if
    index = index + 1
  End While
End   // Event_Start
/************************************************************************
Function    : Event_End
Description : Determines the end point for a cough event by examining the slope and
determining if the pressure has remained relatively unchanged for a certain length of
time.
************************************************************************/
Event_End ( )
   Stop = Find_Level_Pressure ( )
End   // Event_End
/************************************************************************
Function    : Boundarize_Event
Description : Determines the start and end points for a cough event.
************************************************************************/
Boundarize_Event ( )
   CoughStart = Event_Start ( )
   CoughStop = Event_End ( )
End   // Boundarize_Event
/************************************************************************
Function    : Baseline_Pressure
Description : Determines the baseline pressure for a cough event by looking for a
relatively flat pressure for at least a 2 second window prior to the cough event.
************************************************************************/
```

```
Baseline_Pressure ( )
  Start = 0;
  Average = Average_Pressure ( )
  Stop = Find_Level_Pressure (Average)
  If (Stop > (Start + 2 seconds))
    Start = Stop − 2 seconds
  End If
  BaseLinePressure = Average_Pressure (Start, Stop)
End    // Baseline_Pressure
/*************************************************************
Function     : Calibrate
Description  : Allow the user to calibrate the pressure sensors. If voltage levels are
               too low the program will exit.
*************************************************************/
Calibrate ( )
  Voltage = ReadAnalogVolts ( )
  If (Voltage < 14.0)
    Display ("Please replace 9V batteries!")
    Exit Program
  Else If (Voltage >= 14.0)
    Voltage = ReadAnalogVolts ( )
    If (Voltage < 6.0) {
      Display ("Please replace AA batteries!")
      Exit Program
    End If
    Display ("Connect pressure sensors and place in OPEN position.")
    Vp1cal = ReadAnalogDiff(Channel0)
    Vp2cal = ReadAnalogDiff (Channel2)
    Display ("Unit calibrated. Close both pressure sensors.")
  End If
End      // Calibrate
/*************************************************************
Function     : In_Patient_Physiology
Description  : Performs the inpatient physiology algorithm.
*************************************************************/
In_Patient_Physiology (void)
  If (PostVoidResidual > 100.00)
    If (RestingDetrusorPressure > 15.00)
      dispLedOut (RED)
        // UMN Bladder
        // Detrusor/sphincter dyssynergia (DSD)
        // UROLOGY EVAL
    Else If (RestingDetrusorPressure <= 15.00)
      If (MaxVoidingDetrusorPressure > 60.00)
        If (PatientLeaked)
          dispLedOut (YELLOW)
            // Bladder Outlet Obstruction (BOO)
            // Overflow incontinence
            // Possible DSD
          Else
          dispLedOut (YELLOW)
            // Bladder Outlet Obstruction (BOO)
            // Possible DSD
        End If
      Else If (MaxVoidingDetrusorPressure <= 60.00)
        If (PatientLeaked)
          dispLedOut (YELLOW)
            // Overflow incontinence
            // Possible SUI
          Else
          dispLedOut (YELLOW)
            // Atonic bladder
            // Hypotonic bladder
        End If
      End If
    End If
  Else If (PostVoidResidual <= 100.00)
    If (RestingDetrusorPressure > 15.00)
      dispLedOut (YELLOW)
        // Detrusor instability
        // Urge incontinence
        // Mixed incontinence
      Else If (RestingDetrusorPressure <= 15.00)
      If (PatientLeaked)
        dispLedOut (YELLOW)
          // SUI
        Else
        dispLedOut (GREEN)
          // Normal Study
```

```
            End If
         End If
      End If
   End     // In_Patient_Physiology
/*************************************************************************
Function     : Run_RCT_Test
Description  : Performs the steps to run the RCT test.
*************************************************************************/
Run_RCT_Test ( )
   RestingBladderVolume = SetBladderVolume ("Please scan and enter RBV: ")
   Display ("Please place the catheter)
   Display ("Please place the pad")
      Start measuring to establish baseline and DetrusorPressure
   Calculate Resting DetrusorPressure for 30 seconds
   Display ("Please perform iRCT test)
   PostVoidResidual = SetBladderVolume ("Please scan and enter PVR: ")
   PatientLeaked = VerifyLeak ("Did patient leak (Y/N) ?")
   Stop measuring pressures
   Baseline_pressure ( )
   Boundarize_Event ( )
   PeakPressure = Peak_Pressure ( )
   Average = Average_Pressure ( )
   Calculate AreaUnderCurve
   In_Patient_Physiology ( )
   Display ( PeakPressure , Average, AreaUnderCurve)
End     // Run_RCT_Test
//----------------------------------------------------------------
// Main program runs the display with menu.
//----------------------------------------------------------------
main ( )
   Initialize all hardware and parameters
   Init_Arrays ( );
   while (Not Exit)
      Get MenuOption from the user
      If (MenuOption = 1)
         Calibrate ( )
      Else If (MenuOption = 2)
         Run_RCT_Test ( )
      Else If (MenuOption = 3)
         Download measured and calculated data
      Else If (MenuOption = 4)
         Exit Program
      End If
   End While
End     // main
```

FIGS. 30a-30e show a modified device such as that illustrated in the incorporated by reference '257, '281 and '316 applications, but modified to include an active valve as explained relative to FIGS. 19-23 and FIGS. 24-27. A balloon is illustrated in these examples. FIGS. 31a-31f show a passive valve used on the device as in the incorporated by reference applications.

The device may include a pressure "bubble" at the end of the inflation lumen and could include a manometer connected for measuring pressure, for example, at the valve and against the esophageal wall. Another lumen extending through the main body could be included with holes for suction just above the Lower Esophageal Sphincter (LES) to aid in suctioning reflux or emesis. This is advantageous for a surgery patient or acute neural or trauma patient. Details of such device are explained below.

It should be understood that stroke can cause Lower Esophageal Sphincter (LES) weakness. The LES is weakened by stroke and other factors, including the initiation of an involuntary cough such as through the iRCT test. The Ng/Og device, in accordance with a non-limiting example and described in detail below, acts as an esophageal reflux protection device to protect the patient from the weakness of the Lower Esophageal Sphincter (LES). It is known that cough causes reflux, which causes more cough. This is a vicious cycle. This device allows blocking of emesis and prevents reflux associated with pneumonia and anesthesia or other functions affecting neural patients. The Ng/Og device shown in FIGS. 30a-30f can be used when there is microscopic reflux or massive emesis, which both can cause pneumonia.

It should be understood that the esophagus is about 25 centimeters long. It is a muscular tube with a diameter of about 2 centimeters average. It tracks the vertebral column curve and descends through the neck and posterior medistinum and passes through the esophageal hiatus in the right crus of the diaphragm to the left of the median plane at the level of the T10 vertebrae.

The esophagus enters the stomach at the cardial orifice to the left of the midline at the level of the 7th left costal cartilage and T11 vertebra. The abdominal part of the esophagus extends from the esophageal hiatusis in the right crus of the diaphragm to the cardial (cardiac) orifice of the stomach. This area is only about 1.25 cm long.

Food passes through the esophagus rapidly because of the peristaltic action and is typically not dependent on gravity. The esophagus is attached to the margins of the esophageal hiatus in the diaphragm by the phrenicoesophageal ligament, an extension of the inferior diaphragmatic fascia. This ligament permits independent movement of the diaphragm and esophagus during respiration and swallowing. The esophagogastric junction lies to the left of the T11 vertebra on the horizontal plane that passes through the tip of the xiphoid process. Immediately superior to the esophagogastric junction, the diaphragmatic musculature forming the esophageal hiatus functions as a physiological inferior (lower) esophageal sphincter (LES) that contracts and relaxes. The sphincter mechanism for the LES is typically efficient in preventing reflux of gastric contents into the esophagus based on radiological studies. The lumen of the esophagus is normally collapsed superior to this level to prevent food or stomach juices from regurgitating into the esophagus when an individual is not eating.

Barium fluoroscopic studies of the esophagus normally show three constrictions of the esophageal lumen due to impressions from adjacent structures. These are possible locations for placing a device for reflux analysis and GERD treatment.

A first constriction is the cervical constriction (upper esophageal sphincter). The superior aspect of the esophagus is the pharyngoesophageal junction, and is approximately 15 cm from the incisor teeth. The cricopharyngeus muscle creates this cervical constriction, which is located at approximately the level of the sixth cervical vertebra.

A second constriction is the thoracic (broncho-aortic) constriction. The arch of the aorta and the left main bronchus cross the esophagus and create esophageal constrictions as seen on anteroposterior and lateral views, respectively. The constriction caused by the arch of the aorta is 22.5 cm from the incisor teeth and the constriction formed by the left main bronchus is 27.5 cm from the incisor teeth.

A third constriction is the diaphragmatic constriction. The esophageal hiatus of the diaphragm is approximately 40 cm from the incisor teeth and forms the diaphragmatic constriction. This is at the level of the lower esophageal sphincter.

The presence of these constrictions is important when placing the device and its active or passive valve, which would help prevent the reflux of gastric contents into the upper esophagus and pharynx. The placement of the device and valve in one example is suggested inferior to the broncho-aortic constriction (27.5 cm from the incisor teeth), but superior to the diaphragmatic constriction at 40 cm from the incisor teeth. The device typically should not be placed in regions of the esophagus with pathological involvement of the esophagus.

Figure 30A:
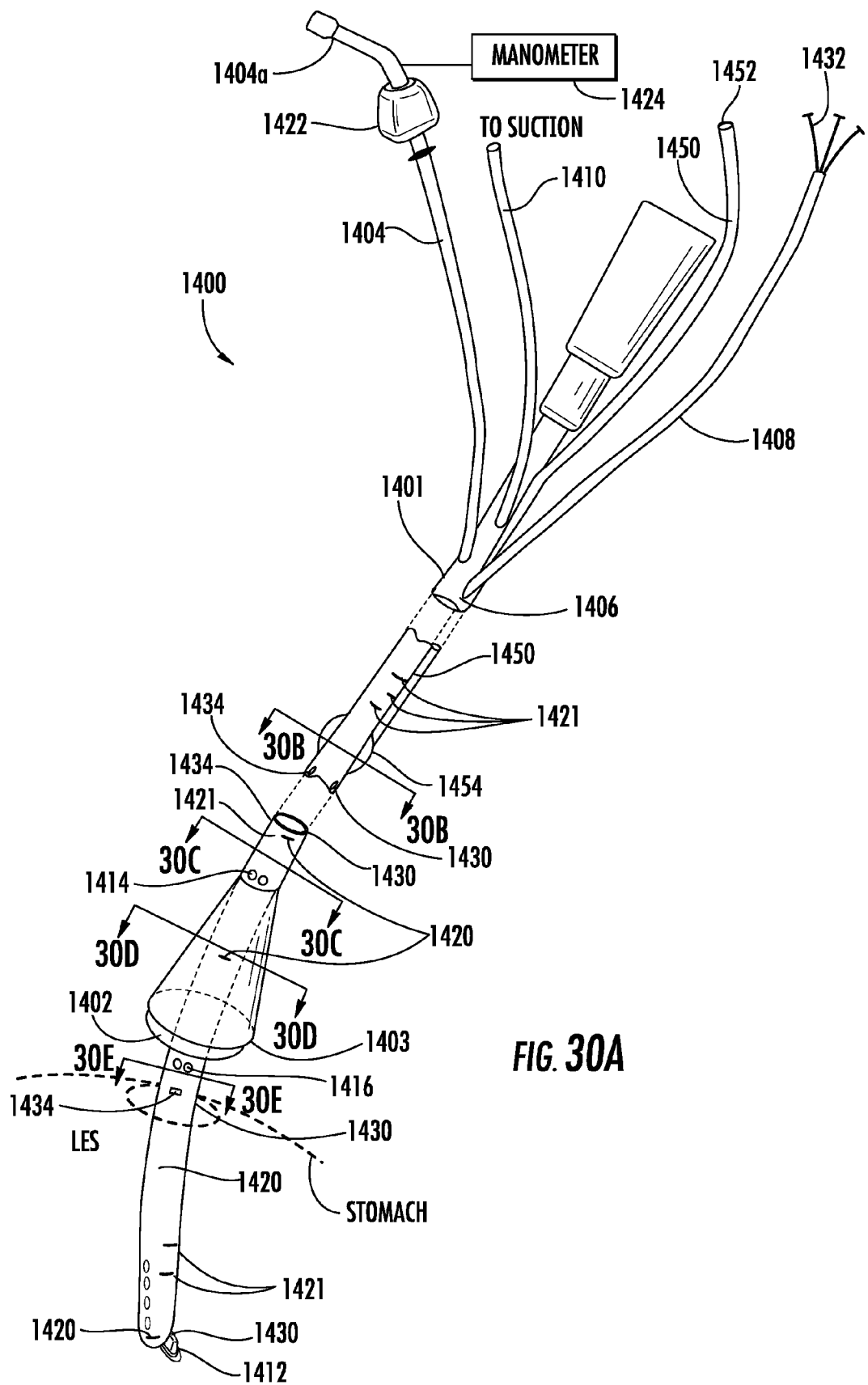
FIGS. 30A through 30F are figures showing an embodiment of an nasogastric/orogastric (Ng/Og) device and having a nebulizing, pH sensing and pressure sensing function and an active valve such as shown in the embodiments of FIGS. 19-27.
Figure 30B:
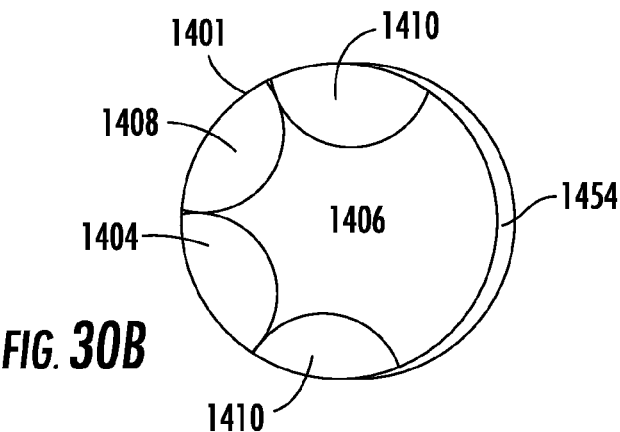
Figure 30C:
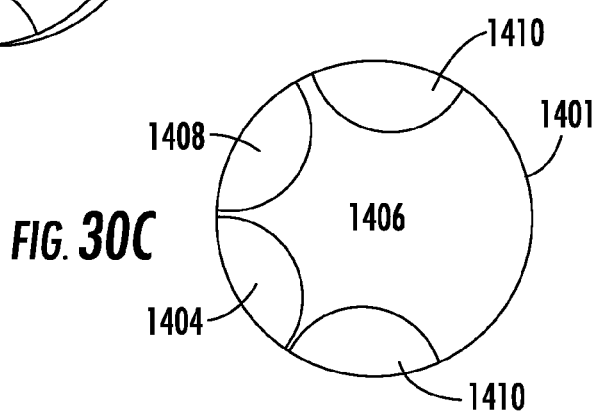
Figure 30D:
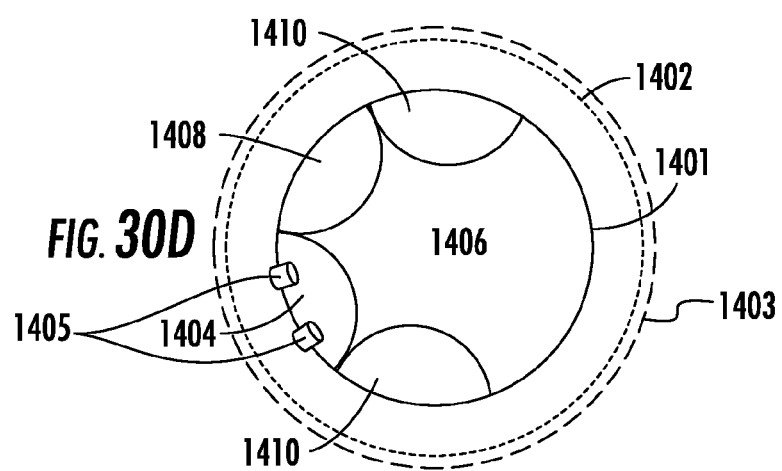
Figures 30E, 30F:
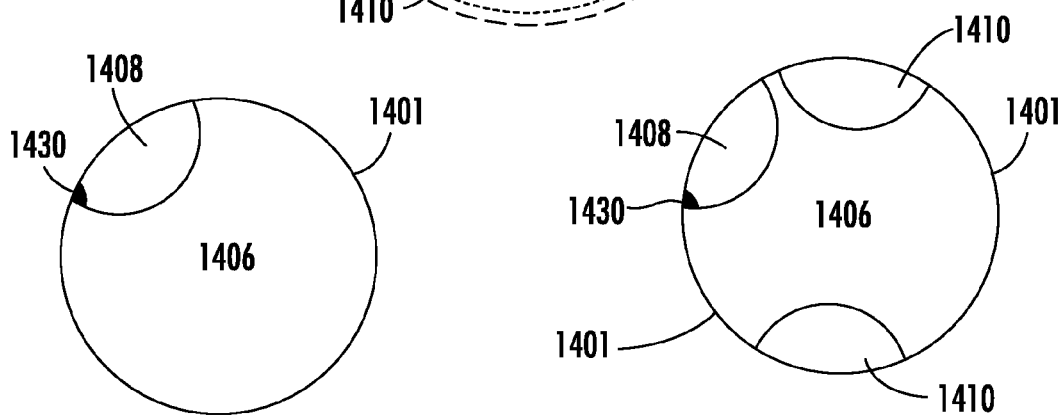
Figure 31A:
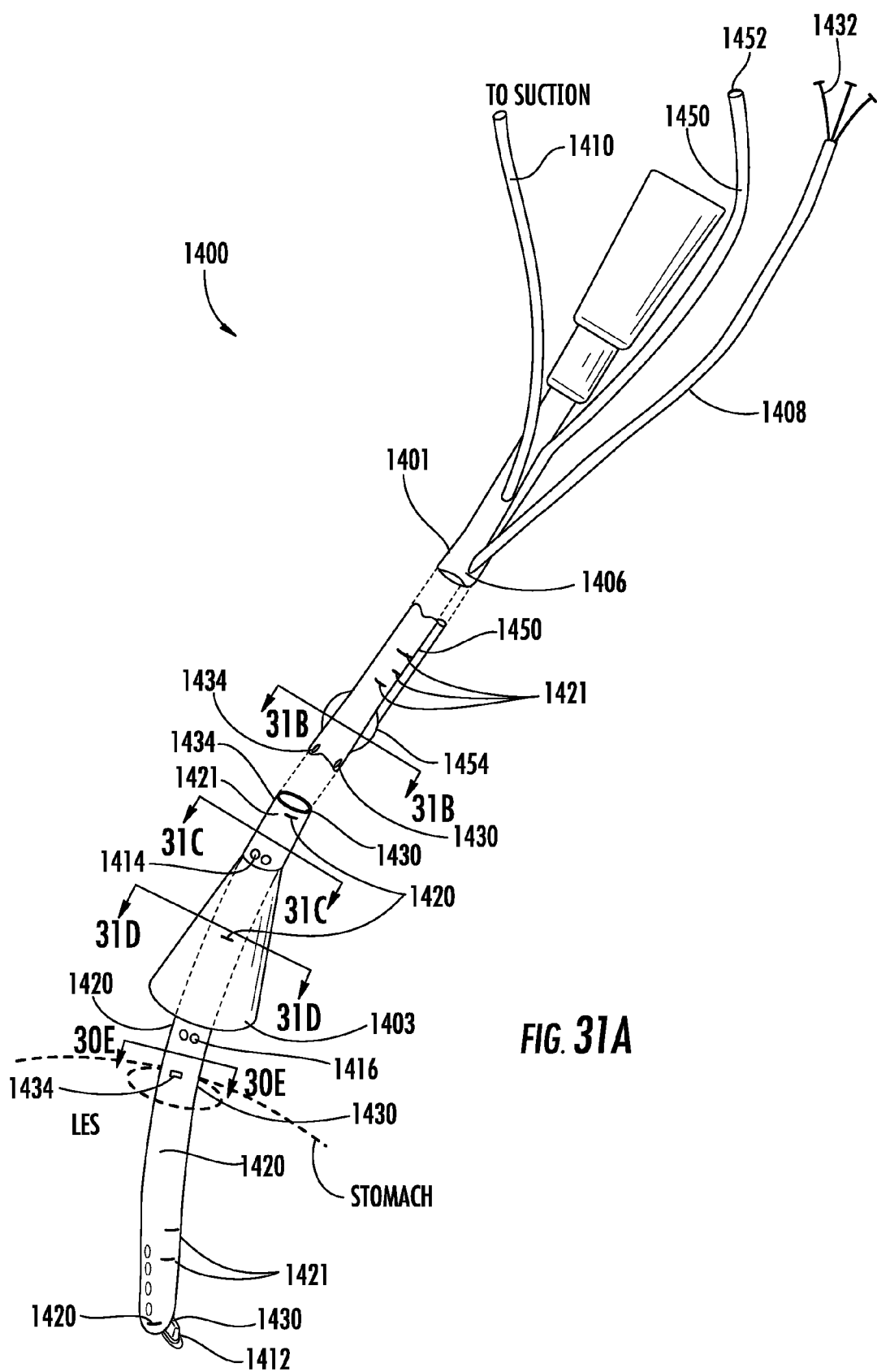
FIGS. 31A through 31F are views similar to those shown in FIGS. 30A-30F but showing instead a device configuration with a passive instead of active valve.
Figure 31B:
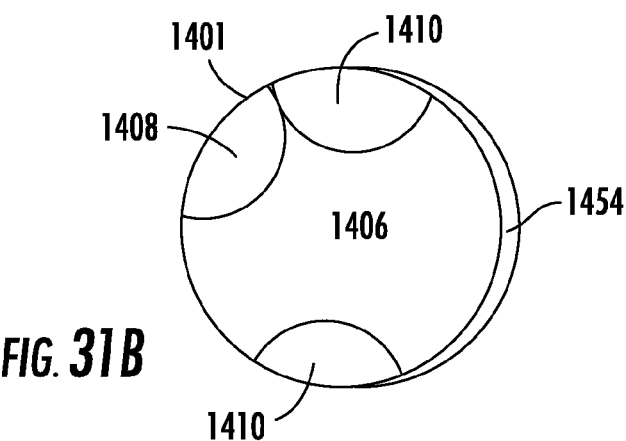
Figure 31C:
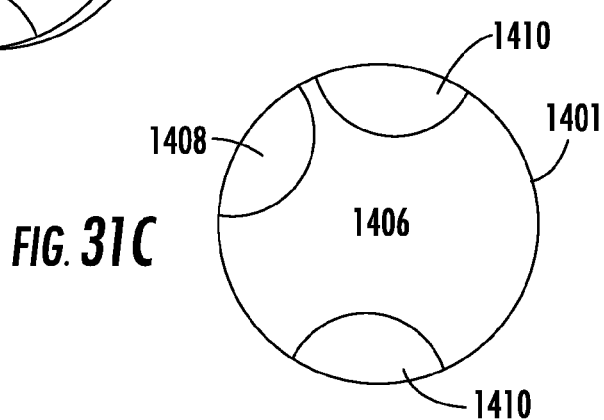
Figure 31D:
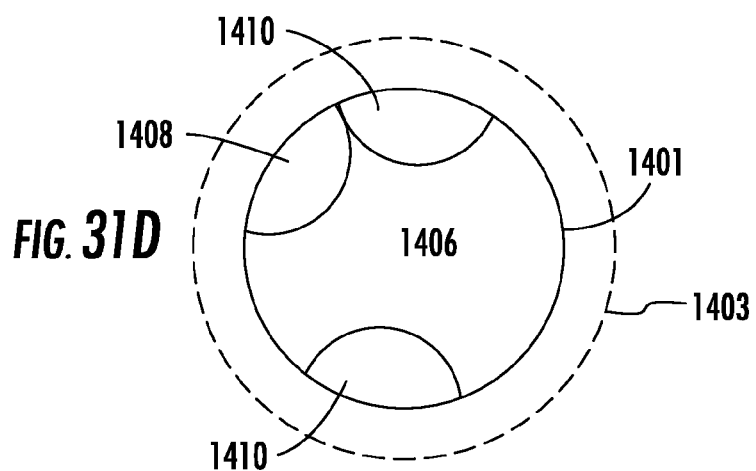
Figure 31F:
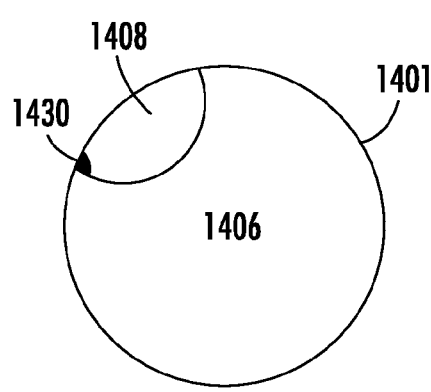
Figure 31E:
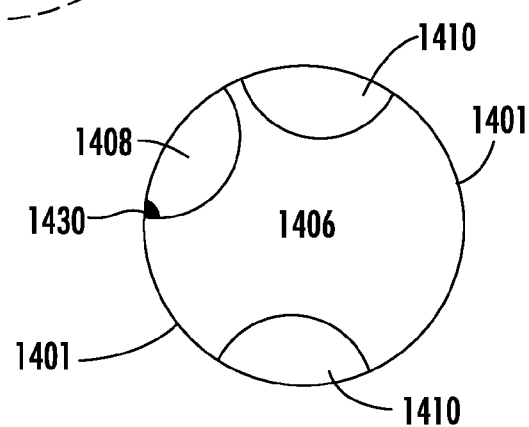

FIGS. 30a-30e show the device in plan and sectional views and indicated generally at 1400, and includes a main device body 1401 and the active valve with a separate inflation lumen 1404 for inflation and deflation of the balloon 1402 positioned under the flexible sheath 1403 as shown in FIG. 30b-30d. FIG. 30d shows the balloon 1402 in dashed lines and inflated. Air channels 1405 connect the inflation lumen and the balloon as shown in FIG. 30d. The section view in FIG. 30e shows the termination of the inflation lumen.

The tip of the device is shown positioned in the stomach, which is shown schematically in FIG. 30a. FIG. 30c is a cross-section taken along line 30c-30c of FIG. 30a. FIG. 30d is a cross-section taken along line 30d-30d of FIG. 30a. FIG. 30e is a cross-section taken along line 30e-30e of FIG. 30a. In these cross-sections, the various lumens are shown, including the main lumen 1406, the sump lumen 1408, the inflation lumen 1404 used for inflating the balloon, and any suction lumens 1410 that are used for suction above the LES. The sump lumen 1408 is connected to a sump port 1412 (FIG. 30a) at the end of the device 1400. Drainage holes 1414 positioned in this example above the valve 1402 allow secretions to pass into the device. These drainage holes could be formed as suction holes and connected to any suction lumens. Suction holes 1416 are positioned below the valve 1402 and connect to the suction lumens 1410 to permit emesis and reflux to be suctioned. The drainage holes could also connect to the suction lumen 1410 as noted before. In a non-limiting example, the drainage holes and suction holes include one-way valves to allow emesis to enter, but not return.

The device can come in variable sizes and lengths depending on patient needs and requirements and typically a standard size for use depending on patients. The device can be used for gastric enteral feedings or gastric decompression resulting from the use of the Salem sump port 1412. The device typically includes radio-opaque markings 1420 throughout the length of the tube as illustrated for measurement and placement. Measured markings 1421 as indicia can be positioned in one example along the length of the tube together with a color changing material or pit sensitive material and at the bulb/cuff for measuring emesis, etc. One radio-opaque marker on the valve itself is used to place the valve about 2 to about 3 cm below the aortic notch.

Inflation and deflation of the balloon in this example is through the luer lock port 1404a for air or fluid entry and exit to form the balloon that includes a pressure balloon 1422 adjacent thereto. The manual pressure balloon 1422 allows for a tactile cuff and a gross pressure check such as through a manometer 1424 attached thereto. The luer lock port 1404a attaches in one example to a manometer for actual cuff pressure measurement. The balloon 1402 easily collapses for emergency removal or self-extubation without causing damage to surrounding structures of the esophagus, hypopharynx, pharynx, and oral cavity. The balloon can be kept inflated below the capillary pressure of the esophageal wall to prevent ischemia that is typically about 7-8 centimeters (cm) water. As indicated before, there are radio-opaque markings 1420 to aid in valve placement confirmation. The inflation/deflation port 1404a can be a different color than the openings for the sump lumen, the suction lumen and the main lumen. The inflation/deflation port 1404a in one example is fitted with the standard luer lock cap and the inflation/deflation port can be labelled with the term "esophageal valve" to aid practitioners in identifying the port.

The Ng/Og device is typically inserted through the nasal cavity or through the oral cavity and enters into the stomach. Measurements can be made from the lips or nares to the TMJ (temporomandibular joint) and to about four-finger breadths to sub-xyphoid. When the balloon is deflated, a water-soluble lubricant can be applied to the end of the device to aid insertion. This Ng/Og device is inserted in a manner similar to an OgT (orogastric tube) or NgT (nasogastric tube) (Ng/Og tube) with the clinician or nurse using the placement radio-opaque markings 1420 to position the device over the lungs and stomach and the valve 2 to about 3 cm below the aortic notch. Once it is in position, it is possible to use auscultate placement by listening to sounds and using an air bolus into the tube and attempt to aspirate gastric contents from the tube. The device is secured and its placement confirmed by x-ray (using the radio-opaque markings 1420 for help) and the preferred location of the valve is inferior to the broncho-aortic constriction while superior to the diaphragmatic constriction. The balloon 1402 is inflated through the inflation lumen 1404 and the balloon pressure may be measured with the manometer 1424. The main lumen 1406 as part of the device body 1401 will have low continuous or intermittent suction and may also be used to administer external feedings.

In accordance with a non-limiting example, the involuntary Reflex Cough Test (iRCT) is used to evaluate the impairment and/or recovery of airway protection. An advantageous pressure for the balloon 1402 and thus flexible sheath against the inside wall of the esophagus is below the esophageal wall capillary pressure. The use of the involuntary reflex cough test is advantageous for people who are neurologically impaired to check to see if they can protect their airway. In this particular device example, pressure sensing is used in conjunction with the device. EMG determination can also be used, as well as pH sensing. Any transceiver inputs for pressure, pH or EMG could input directly into the handheld device. For example, the device could carry pressure sensors as pressure transducers 1430 at various locations on the device to measure pressure when the device is inserted within the esophagus. The transducers 1430 could have transducer leads 1432 that extend through the sump lumen 1408 or be embedded in a wall of the main tube or one of the other lumens. One pressure sensor or transducer 1430 could be in the stomach (such as at the sump lumen), another at the LES, another at mid-esophageal and/or another at the superior esophageal location. It is possible to use an air charged catheter as a pressure sensor with a separate lumen for determining pressure in the stomach, which can be used to determine intra-abdominal pressure. An air charged catheter would require some calibration. Other sensors as non-limiting examples could use fiber optic or other circuit means. The intra-abdominal pressure can be measured but also intra-thoracic pressure. Reflux can be measured by having pH sensors 1434 as inputs along the side with leads also extending through the sump lumen in this example. The handheld device can connect by wired connection or wireless connection to the various pressure, pH and EMG sensors, probes, pads, transducers, etc. It should also be understood that the catheter can be coated with a color changing material, such as for indicating the extent of acid reflux or emesis.

The device includes a nebulizer lumen 1450 that is extralumenal to the main device body 1401 and provides a nebulizer function using a separate nebulizer port 1452 from the main lumen. This nebulizer port 1452 connects to an oxygen or air source for delivering medication such as for the involuntary reflex cough test at the esopheryngeal area for inhalation into the pulmonary tree or medicine for treating a patient. As illustrated, the nebulizer lumen 1450 terminates at a nebulizer structure or nebulizer/medication delivery mechanism having a built-in venturi 1454 to allow delivery of medication for the iRCT around a portion or all the main device body 1401 forming the tube.

FIG. 30b shows a cross-section taken along line 30b-30b and showing the venturi of the nebulizer and the main lumen 1406, deflation/inflation lumen 1404, suction lumen 1410, and sump lumen 1408. The two suction lumens 1410 may merge near the proximal portion of the main body or be separate and provide either common suction at the same time above and below the cuff or individually controlled suction. The suction holes or ports as noted before include one-way valves to allow fluid into the suction lumen 1410, but not out. The valves could be formed as cut flaps that extend inward, but not outward to allow ingress, but not egress. This is advantageous such as when emesis extends upward around the tube from the stomach and can pass into the tube to be suctioned, but not passed back out. Also, secretions, if they get past the cuff, will be suctioned by the suction ports that are located above the cuff as illustrated.

The pressure transducers 1430 are located at various points such as at the distal tip at the sump to measure intra-abdominal pressure. A pressure transducer 1430 can be located below the cuff 1430 and above the cuff 1402 with leads extending through the sump lumen 1408 and connected to the handheld device. A pressure transducer 1430 in one example is located at the sump lumen (FIG. 30f). As noted before, it is also possible to include pH sensors 1434 on the device that include leads extending through the sump lumen 1408, allowing pH to be measured to detect when emesis is rising from the stomach. The pH sensors 1434 could be located at different locations such as below the cuff and above the cuff and even farther up along the main device body 1401. The coating on the device could indicate pH.

This Ng/Og device as illustrated in FIGS. 30a-30f is a multi-purpose Ng/Og device that can be used in a variety of patients who are at risk for aspiration of gastric contents, elevated intra-abdominal and/or intra-esophageal pressures, and/or abnormal airway protection. The device is not limited to the illustrated embodiments, but can be configured with all or any variation in combination of different components to fit the needs of the patient.

An esophageal suction port 1416, which in this embodiment is below the valve, but could also be positioned above the valve together with or below the valve, permits suction to occur and uses one-way port holes that are located above and below the esophageal cuff such that emesis, reflux and other material can be sucked into the suction lumen 1410 but not pass out. Any suction ports 1416 open with the administration of low pressure and intermittent suction. Low suction can be applied to remove the refluxed gastric material in the lower esophagus below the valve. The low suction can also be applied to remove material such as, but not limited to, oral or nasal secretions, medications and/or tube feeding material that is collected in the esophagus above the esophageal cuff. For purposes of identification to the nurse or other practitioner, it can be labelled as "Intra-Esophageal Access: Do Not Instill."

The nebulizer venturi 1454 will typically be positioned at the level of the larynx between the nasal pharyngeal area/oral pharyngeal area and allow medication to be administered. The device can be used to measure both intra-abdominal hypertension and reflux. The dimensions of this device are not larger than a regular Ng/Og tube and not larger than 18 to about 20 French in one example. The sump lumen is much smaller as compared to the main tube, but in this example, large enough to accommodate various leads, which could extend through other lumens. The sump lumen, however, typically remains more clean.

The device is also a fully functioning feeding tube for food, liquids or medicine to the stomach and acts as a separate reverse channel, to allow suctioning below the LES in the stomach, and the possibility for constant low-pressure suctioning for reflux above the LES. In a preferred example, the device collapses with pulling even if it is not deflated and pulled by a patient for safety. As noted before, xrays can be used to aid placement of the device in the esophagus by viewing the radio-opaque marker on the valve. This device can be engineered as necessary for any severe neuro functions and risks for LES weakness or increased LER activity because of dysphagia or reflux, and protect general anesthesia patients after extubation. The device is useful for iRCT testing and protects the patient from neutral created anti-acid medicine stomach content reflux that might get past the ASIC receptors or RAR's (retinoic acid receptors).

The device as described has many different advantageous uses. The top portion of the device includes different ports and non-ports, all operating together as an Ng/Og tube for oral or nasal uses. This device also can test reflex cough and deliver micro-nebulized medicines, such as disclosed in the commonly assigned U.S. patent application identified also.

In the past, Ng/Og tubes were not used with a patient that could not protect their airway. This protective NG/OG device as described, however, in accordance with a non-limiting example, is safely used with a patient that cannot protect their airway and especially useful when administering the iRCT in case reflex occurs. The device can be left in a patient for protection.

FIGS. 31a-31e show a device similar to that shown in FIGS. 30a-30f except a passive valve is used and there is no balloon and no need for an inflation lumen and none are illustrated as shown in the various cross-section views. The same description applies except balloon pressure concerns are not necessary. There is also no requirement for the manual pressure balloon and manometer, and none are illustrated.

For purposes of technical understanding, some description of the involuntary reflex cough test is set forth.

The induced reflex cough test (iRCT) activates the nucleus tractus solitarius (NTS), as compared to the voluntary reflex cough test. The iRCT selectively activates neurons in or adjacent to the NTS. The NTS conveys impulses to brainstem and spinal cord motor nuclei that stimulate muscles involved in expiration (expiration) associated with the laryngeal expiratory reflex (LER), i.e., involuntary cough. In the brainstem the NTS conveys impulses to the nucleus ambiguous, which controls opening and closing of the glottis of the larynx. In the spinal cord, descending impulses from the NTS will stimulate neurons in or adjacent to the Medial Motor Cell Column (MMCC). The MMCC will control paraspinal muscles, expiratory muscle of the trunk, e.g., external abdominal oblique muscles, and pelvic floor musculature. The LER motor pattern elicited by the iRCT is a bilaterally symmetrical and synchronized motor event. In the past, urologists did not selectively activate MMCC without overtly activating spinal neurons of the lateral motor cell column (LMCC), which are associated with limb musculature. Magnetic stimulation or electrical spinal cord stimulation activates both MMCC and LMCC and thus it is not possible to sort out pathology with these tests. Magnetic stimulation or other approaches from CNS activation also activate both columns.

The induced reflex cough test (iRCT) activates the LER, which is essential for clearing the upper airway of potential aspirants during eating or inhalation. The LER elicits contraction of the abdominal muscles, which compresses the abdominal structures and thereby increases intra-abdominal pressure (IAP) and displaces the diaphragm superiorly. During this natural abdominal compression, the upward displacement of the diaphragm will generate the cough force necessary to clear the upper airway and also increase the pressure inside the urinary bladder (intravesicular pressure). During this motor event involving an increase in IAP, all intrinsic sphincters of the abdomen (e.g., lower esophageal sphincter (LES)) and pelvis urethral and anal sphincters must be physiologically closed. If these sphincters are not closed during a LER involuntary cough episode, the individual may have gastro-esophageal reflux (GER) and/or urinary and/or fecal incontinence.

The laryngeal expiratory reflex (LER) is a brainstem-mediated reflex that initiates an immediate series of expiratory coughs without an inspiratory phase. The LER is the involuntary reflex that neurologically protects the upper airway from noxious aspirants and, as such, it has a critical neurological function, which is unique to humans. The induced reflex cough test (iRCT) can be triggered such as by using a nebulized 20% solution of a mild chemoirritant to elicit in patients a LER. The iRCT is characterized by a series of, at least, five expiratory reflex coughs (C5) with a typical 17 ms latency to the external abdominal oblique (EAO) muscles. During the LER, contraction of the EAO muscles compress the abdominal viscera, which push against the relaxed diaphragm superiorly for the expiratory phase and push inferiorly against the urinary bladder and rectum, with a concomitant increase in intra-abdominal pressure (LAP).

Since reflex cough is expiratory and is not preceded by diaphragmatic contraction associated with inspiration, the iRCT indicates the native tonicity and function of the urethral sphincter (US) and lower esophageal sphincter (LES), which is typically critical in the diagnosis of SUI and GERD, respectively. Animal models cannot adequately study the voluntary cough (VC) and the LER, since the animals are surgically decerebrated and intubated.

This application is related to copending patent application entitled, "DEVICE WITH ACTIVE VALVE TO BLOCK EMESIS AND REFLUX BLOCKAGE DEVICE AND ASSOCIATED SYSTEM AND METHOD," which is filed on the same date and by the same assignee and inventors, the disclosure which is hereby incorporated by reference.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A system for diagnosing a physiological abnormality in a patient, comprising:
   a tube insertable into the esophagus;
   a valve carried by the tube and comprising a flexible sheath having an upper circumferential edge secured onto the tube and an unsecured lower circumferential edge and configured such that upon contact with emesis and/or reflux from the stomach, the flexible sheath opens in a concave configuration towards the stomach and the unsecured lower circumferential edge engages the esophageal wall and blocks emesis and/or reflux from the stomach passing into the esophagus past the valve to protect a patient's airway during an involuntary reflex cough event;
   a port through which medication is delivered for administering the involuntary reflex cough event;
   a pressure sensor carried by the tube and configured to measure intra-abdominal pressure (IAP) during the involuntary reflex cough event;
   an electromyogram (EMG) pad configured to obtain an EMG from involuntary cough activated paraspinal muscles; and
   a processing device connected to the pressure sensor and the EMG pad and configured to receive the IAP and EMG and correlate the IAP and EMG with the involuntary reflex cough event to determine a physiological abnormality.

2. The system according to claim 1 comprising a second pressure sensor carried by the tube, and said processing device correlates sensed pressure from the second pressure sensor with the IAP and EMG.

3. The system according to claim 1 comprising a pH sensor carried by the tube and said processing device correlates pH measurements from the pH sensor with the IAP and EMG.

4. The system according to claim 1 wherein said processing device comprises a housing and an interface to receive measurements from the at least one sensor obtained during the involuntary reflex cough event and a processor carried by the housing and configured to receive the measurements from the at least one sensor obtained during the involuntary reflex cough event.

5. The system according to claim 1 wherein said tube has a distal and proximal end and configured for insertion through a patient's esophagus such that the distal end is received within the patient's stomach, and a sump lumen extending the length of the tube and a sump port at the distal end of the tube and communicating with the sump lumen and configured to vent gas.

6. The system according to claim 1 wherein said valve is positioned on the tube to be mid-esophagus below the aortic notch when the tube is received through the esophagus, and a radio-opaque marker carried by the valve to aid in positioning the valve mid-esophagus.

7. The system according to claim 6 wherein said valve is configured to be positioned at about 2 to about 3 cm below the aortic notch when the tube is received through the esophagus.

8. The system according to claim 1 wherein said flexible sheath is formed from a multiple density flexible material with the closed position as a normal state, and the material forming the unsecured lower circumferential edge is formed to minimize damage to the esophageal wall as it makes contact therewith.

9. The system according to claim 1 wherein said tube is formed of multiple lumens and including a lumen for suction.

10. The system according to claim 1 and further comprising a nebulizer lumen extending along the tube.

11. A method for diagnosing a physiological abnormality in a patient, comprising:
    inserting a tube into the esophagus and having a valve carried by the tube comprising a flexible sheath having an upper circumferential edge secured onto the tube and an unsecured lower circumferential edge and configured such that upon contact with emesis and/or reflux from the stomach, the flexible sheath opens in a concave configuration towards the stomach and the unsecured lower circumferential edge engages the esophageal wall and blocks emesis and/or reflux from the stomach passing into the esophagus past the valve to protect a patient's airway during an involuntary reflex cough event;
    administering a nebulized medication to the patient to activate the involuntary reflex cough event;
    obtaining an electromyogram (EMG) from involuntary cough activated paraspinal muscles;
    sensing intra-abdominal pressure (IAP) during the involuntary reflex cough event from a sensor carried by the tube; and
    correlating, by a processing device, the EMG and IAP with the involuntary reflex cough event to determine a physiological abnormality.

12. The method according to claim 11 and further comprising sensing pressure from a second pressure sensor carried by the tube and correlating, by the processing device, the sensed pressure from the second sensor with the EMG and IAP.

13. The method according to claim 11 and further comprising sensing pH from a pH sensor carried by the tube and correlating, by the processing device, the sensed pH with the EMG and IAP.

* * * * *

UNITED STATES PATENT AND TRADEMARK OFFICE
CERTIFICATE OF CORRECTION

PATENT NO. : 9,005,122 B2
APPLICATION NO. : 13/767900
DATED : April 14, 2015
INVENTOR(S) : Addington et al.

Page 1 of 1

It is certified that error appears in the above-identified patent and that said Letters Patent is hereby corrected as shown below:

In the Specification

Column 25, Line 14    Delete:
"3 em"

Insert:
-- 3 cm --

Signed and Sealed this
Twenty-eighth Day of July, 2015

Michelle K. Lee
*Director of the United States Patent and Trademark Office*